(12) United States Patent
Lenna et al.

(10) Patent No.: US 8,242,291 B2
(45) Date of Patent: Aug. 14, 2012

(54) PROCESS FOR THE PREPARATION OF RAMELTEON

(75) Inventors: Roberto Lenna, Legnano (IT); Cristina Ghidoli, Arluno (IT); Luigi Panza, Como (IT)

(73) Assignee: Industriale Chimica S.r.L., Milano (IT)

( * ) Notice: Subject to any disclaimer, the term of this patent is extended or adjusted under 35 U.S.C. 154(b) by 384 days.

(21) Appl. No.: 12/580,909

(22) Filed: Oct. 16, 2009

(65) Prior Publication Data

US 2010/0234622 A1 Sep. 16, 2010

(30) Foreign Application Priority Data

Mar. 10, 2009 (WO) .................. PCT/IT2009/000088

(51) Int. Cl.
*C07D 307/93* (2006.01)
(52) U.S. Cl. ........................................ 549/458
(58) Field of Classification Search ............ 549/458
See application file for complete search history.

(56) References Cited

FOREIGN PATENT DOCUMENTS

EP 1199304 4/2002

OTHER PUBLICATIONS

Denise C. Rodrigues, Sergio A. Fernandes and Anita J. Marsaioli; "Predicting the Claisen Rearrangement Regioselectivity of Allylindanyl and Allyltetrahydronaphthalenyl Ether Derivatives by 1H NMR Experiments"; Magnetic Resonance in Chemistry; 2000; pp. 970-974.

Toru Yamano, Masayuki Yamashita, Mari Adachi, Mitsutaka Tanaka, Kiyoharu Matsumoto, Mitsuru Kawada, Osamu Uchikawa, Kohji Fukatsu and Shigenori Ohkawa; "Approach to the Stereoselective Synthesis of Melatonin Receptor Agonist Ramelteon Via Asymmetric Hydrogenation"; Elsevier Ltd.; 2005; pp. 184-190.

Osamu Uchikawa et al.; Synthesis of a Novel Series of Tricyclic Indan Derivatives as Melatonin Receptor Agonists; J. Med. Chem.; 2002; p. 4222-4239.

K. Chilman-Blair et al.; Treatment of Insomnia Treatment of Circadian Rhythm Disorders Melatonin MT/MT Agonist; Drugs of the Future; 2003; p. 950-958.

*Primary Examiner* — Taofiq A Solola
(74) *Attorney, Agent, or Firm* — Stetina Brunda Garred & Brucker

(57) ABSTRACT

A process is described for the preparation on an industrial scale of N-[2-(8S)-1,6,7,8-tetrahydro-2H-indeno[5,4-b]furan-8-yl]ethyl]propionamide, ramelteon, having the structure illustrated below:

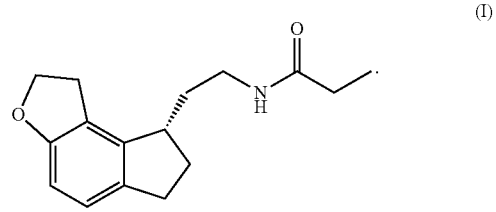

13 Claims, 2 Drawing Sheets

FIGURE 1B

Area Percent Report

```
Sorted By         :    Signal
Multiplier        :    1.0000
Dilution          :    1.0000
Use Multiplier & Dilution Factor with ISTDs
```

Signal 1: DAD1 A, Sig=222,4 Ref=800,100

| Peak # | RetTime [min] | Type | Width [min] | Area [mAU*s] | Height [mAU] | Area % |
|---|---|---|---|---|---|---|
| 1 | 15.574 | BB | 1.6536 | 1.49831e4 | 128.19214 | 100.0000 |

Totals :                           1.49831e4   128.19214

Signal 2: DAD1 B, Sig=288,4 Ref=800,100

| Peak # | RetTime [min] | Type | Width [min] | Area [mAU*s] | Height [mAU] | Area % |
|---|---|---|---|---|---|---|
| 1 | 15.572 | BB | 1.6180 | 6817.19971 | 58.65319 | 100.0000 |

Totals :                           6817.19971   58.65319

\*\*\* End of Report \*\*\*

PROCESS FOR THE PREPARATION OF RAMELTEON

CROSS-REFERENCE TO RELATED APPLICATIONS

Not Applicable

STATEMENT RE: FEDERALLY SPONSORED RESEARCH/DEVELOPMENT

Not Applicable

FIELD OF THE INVENTION

The present invention refers to the field of processes for the synthesis of molecules with pharmacological activity, and in particular a process for the preparation on an industrial scale of the compound N-[2-(8S)-1,6,7,8-tetrahydro-2H-indeno[5,4-b]furan-8-yl]ethyl]propionamide; this compound is known in the sector under the name ramelteon and is used in the treatment of sleep disorders in general and insomnia in particular.

PRIOR ART

Ramelteon, having the structural formula (I) illustrated below,

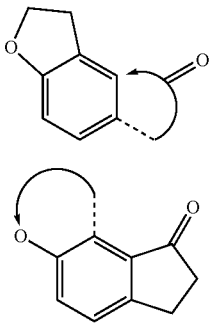

(I)

is a product known in literature and was described for the first time, with relative synthesis, in the patent EP 885210 B1 to Takeda Chem. Ind.

The starting products for the preparation of ramelteon can be 2,3-dihydrobenzofuran or 6-hydroxy-indanone. The cyclisation for formation of the third ring can therefore follow two paths:

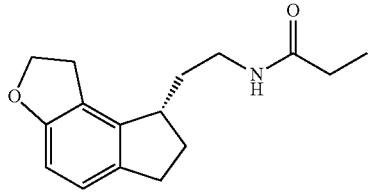

(1)

(2)

The amine function is introduced by Wittig reaction on an intermediate of type (3) followed by reduction of the —C≡N group to give an intermediate of type (4):

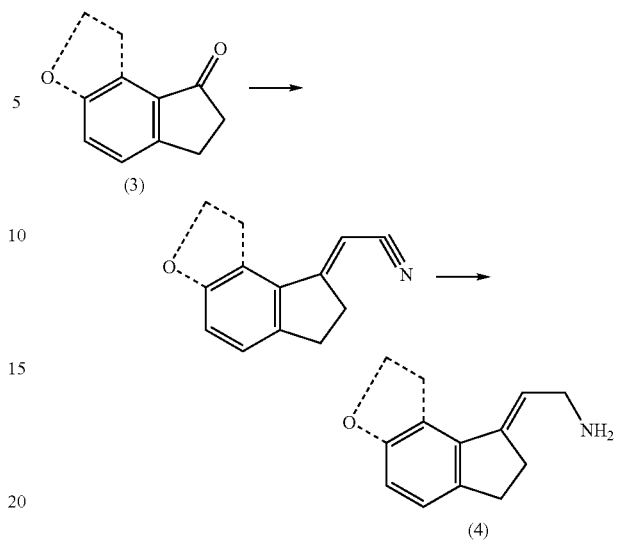

(3)

(4)

Reduction of the double bond resulting in position 8 in the intermediate (4) must provide the end product with stereochemistry S. For this purpose chiral catalysts can be used, or achiral catalysts with subsequent separation of the mixture obtained.

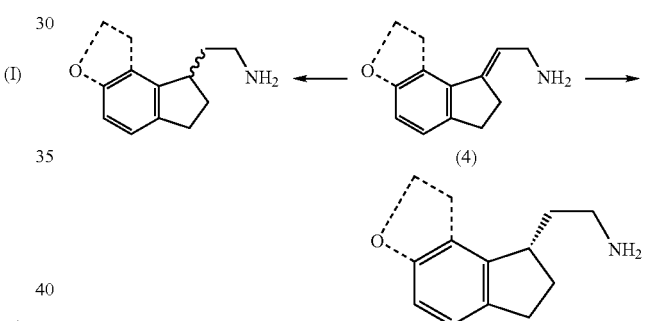

(4)

The transformation from amine to amide occurs in the usual way, with the use of chloride of the acid in the presence of an organic base, and is schematised by the following reaction:

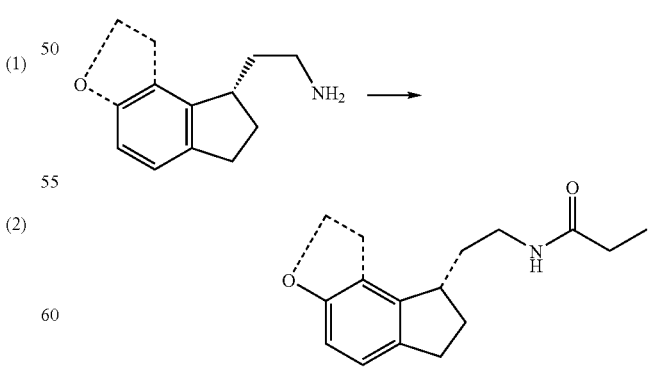

One of the critical points of the synthesis pathways of optically active products like ramelteon is control of the process stereochemistry in order to obtain the desired product with correct spatial arrangement of all the atoms.

In EP 885210 B1, as described in the experimental part, two pathways are followed to obtain the above.

According to the first pathway, illustrated in paragraph [380], example 11, the ramelteon is optically resolved by preparative HPLC with chiral column working on a small amount of product. The example gives data of $[\alpha]_D^{20}$, melting point and NMR without, however, providing the most indicative datum, i.e. the enantiomeric excess, of the product obtained. The indication "optically resolved", in the absence of a numerical datum, does not clarify to what extent the ramelteon has been resolved, and therefore the text in this regard does not give exhaustive indications on the possibility of resolving the racemic mixture via this pathway. Furthermore, the option of resolution on a chiral column is clearly of analytical interest only and has no application for production on an industrial scale.

The second possibility described in EP 885210 B1, in the reference examples 20, 21 and 22, tackles the problem in a different way, intervening on the synthesis. In this case hydrogenations are performed with chiral catalysts, obtaining reduction products with enantiomeric excess (e.e.) up to 90%. The reference example 20, paragraph [302], obtains an e.e. of 100%, but only after repeated crystallisations starting from an e.e. of 88.8%. From the experimental procedures of the examples cited it can be observed that the hydrogenation pressure varies between 50 and 100 bar. Such high pressure values, which already at laboratory level require specific equipment, cannot be easily applied to ordinary plant reactors; rather, they require specific dedicated and constantly controlled reactors.

A similar observation can be made with regard to the reference example 29, paragraphs [310] and [311], in which the intermediate (E)-N-[2-(6-methoxyindan-1-ylidene)ethyl]propionamide is hydrogenated at 70° C. and at a pressure of 90 bar; in this example an e.e. of 99% is reached after chromatographic purification and crystallisation. From the stereochemical point of view the result is more than satisfactory except that it is obtained on one of the first intermediates of the synthesis. This means that the short column chromatography described in paragraph [311] is such and can be performed with ordinary equipment only at laboratory level; it certainly does not apply in the case of industrial production.

The article "Approach to the stereoselective synthesis of melatonin receptor agonist ramelteon via asymmetric hydrogenation", Toru Yamano et al., Tetrahedron: Asymmetry, vol. 17 (2006), 184-190, which was published roughly ten years after the patent EP 885210 B1, describes purification of the asymmetric hydrogenation products of some substrates (indicated as 3, 4a and 4b) and shows how the technique illustrated always requires a final chromatographic purification (see in particular hydrogenation of substrate 3, performed on a few mg, and substrate 4a). In the conclusions of the article the results obtained are defined as encouraging for the development of more efficient processes.

Lastly, the recent patent application EP 1792899 A1 describes a synthesis of (S)-2-(1,6,7,8-tetrahydro-2H-indeno[5,4-b]furan-8-yl)ethylamine with a high degree of purity, applicable industrially and characterised by high process yields. This application touches on another crucial aspect of synthesis of pharmaceutical products, i.e. the impurities generated by the synthesis itself. The description of said (numerous) impurities is detailed, the structures are given in full and their final content in the ramelteon is good, each being below 0.15%, but the method of obtaining the results appears complicated and costly. As described in example 2, the process comprises a double hydrogenation on (E)-2-(1,6,7,8-tetrahydro-2H-indeno[5,4-b]furan-8-ylidene)ethylamine with two different catalysts followed by a crystallisation, then transformation, in a separate operation, of the amine thus obtained to propionamide (i.e. ramelteon) and further purification.

It is therefore evident that there is still the need to develop production processes for ramelteon which are alternative to the known processes and are simpler to apply on an industrial scale.

SUMMARY OF THE INVENTION

One object of the present invention is therefore to provide a process for the synthesis of ramelteon which is industrially applicable without the need for special plants and which, at the same time, allows the compound to be obtained in a pharmaceutical quality and with high yields in a simple manner, limiting re-processing and chromatography.

A further object of the invention is to provide a process for the synthesis of ramelteon which comprises more practical stereoselective reductions than those previously known.

These and further objects are obtained according to the present invention with a process for the preparation of N-[2-(8S)-1,6,7,8-tetrahydro-2H]-indeno[5,4-b]furan-8-il]ethyl]propionamide (ramelteon) of formula (I)

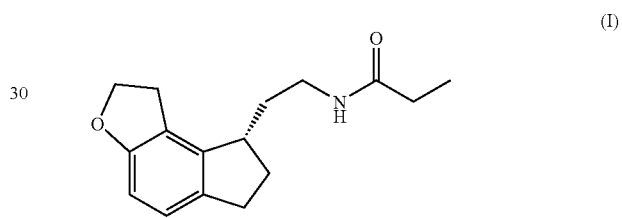

comprising the following reactions:

a) alkylation of the hydroxyl of 6-hydroxy-indanone, (II), to obtain 6-allyloxy-indan-1-one, (III):

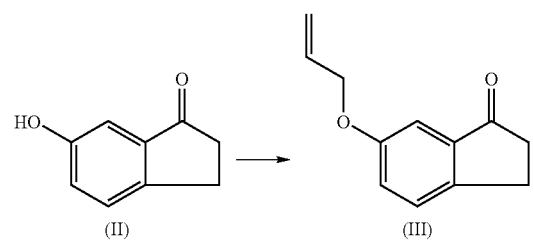

b) thermal Claisen rearrangement on (III) to obtain 7-allyl-6-hydroxy-indan-1-one, (IV):

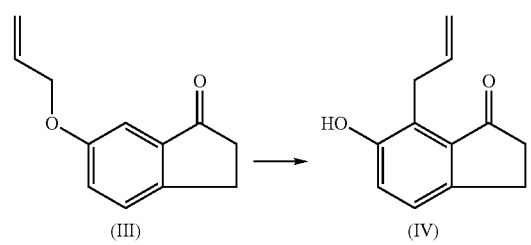

c) protection of the free hydroxyl of (IV) to obtain an intermediate of formula (V):

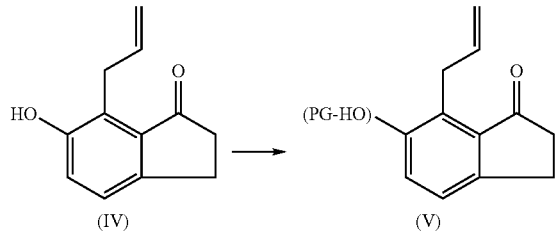

in which (PG-OH) indicates the hydroxyl group protected with a protective group stable in a basic environment;

d) reaction of the intermediate of formula (V) with a dialkyl cyano methylphosphonate to obtain an intermediate of formula (VI)

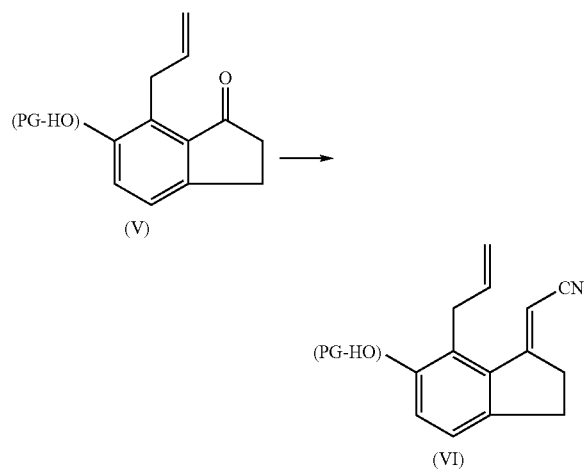

Having obtained an intermediate of type (VI) two synthesis pathways can be followed: a sequence (indicated below as e→f→g→h→i) in which the reaction e is enantioselective; or a sequence (indicated below as E→F→G→H→I) in which the reaction I is enantioselective.

Sequence e→f→g→h→i e) enantioselective reduction on the intermediate of formula (VI), to obtain an intermediate of formula (VII)

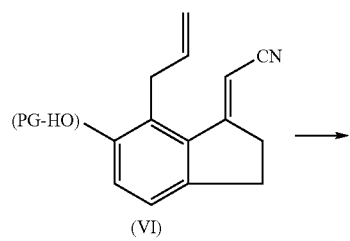

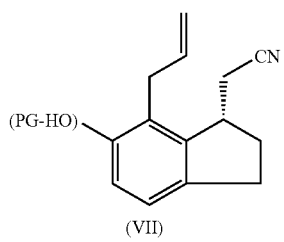

f) oxidative demolition of the double bond of the intermediate of formula (VII), to obtain an intermediate of formula (VIII):

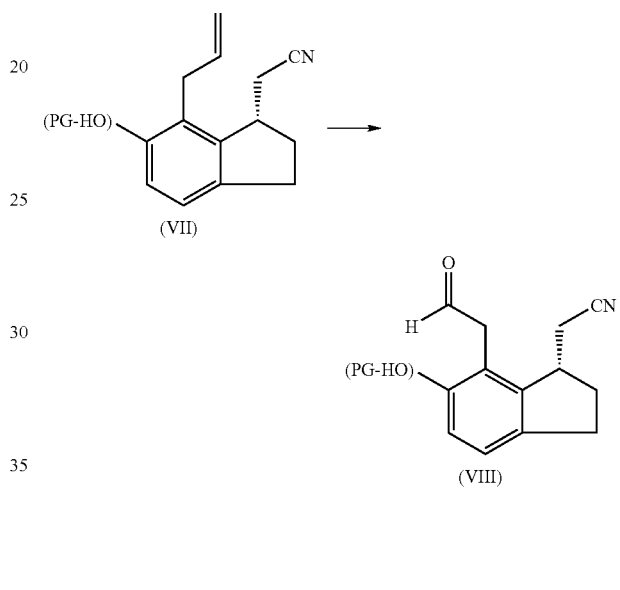

g) reduction of the carbonylic function present in the intermediate of formula (VIII), to obtain an intermediate of formula (IX):

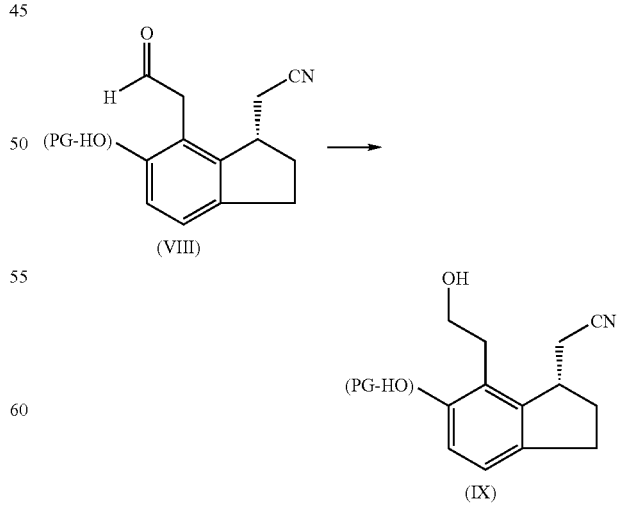

h) transformation of the free hydroxylic group present in the intermediate of formula (IX) in order to make it a good leaving group, to obtain an intermediate with general formula (X), in which (LG) indicates a leaving group:

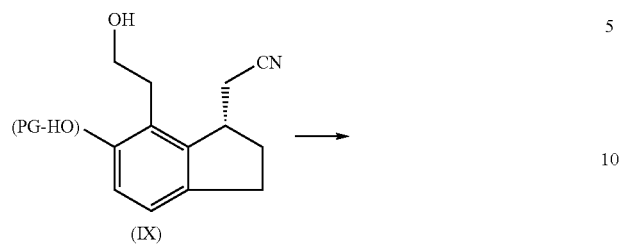

i) intramolecular cyclisation of the intermediate of formula (X) to obtain (1,6,7,8-tetrahydro-2H-indeno[5,4-b]furan-8-yl)acetonitrile, (XI):

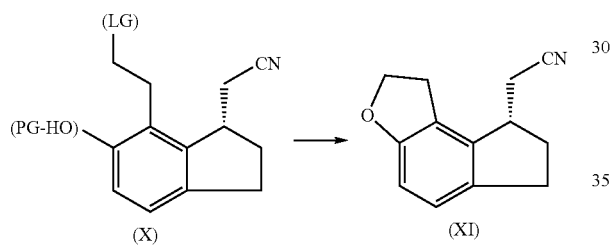

Sequence E→F→G→H→I

E) selective oxidative demolition of the terminal double bond on the intermediate of formula (VI), to obtain an intermediate of formula (7):

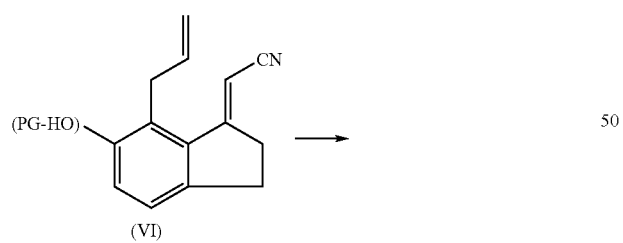

F) reduction of the carbonylic function present in the intermediate of formula (7), to obtain an intermediate of formula (8):

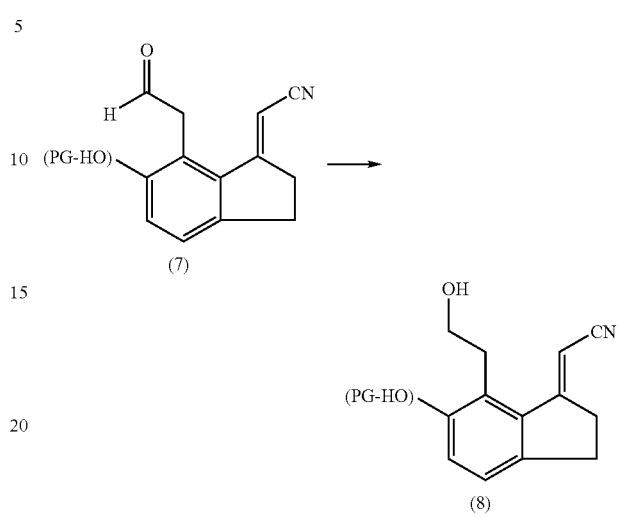

G) transformation of the free hydroxylic group present in the intermediate of formula (8) in order to make it a good leaving group, to obtain the intermediate of formula (9), in which (LG) indicates the leaving group:

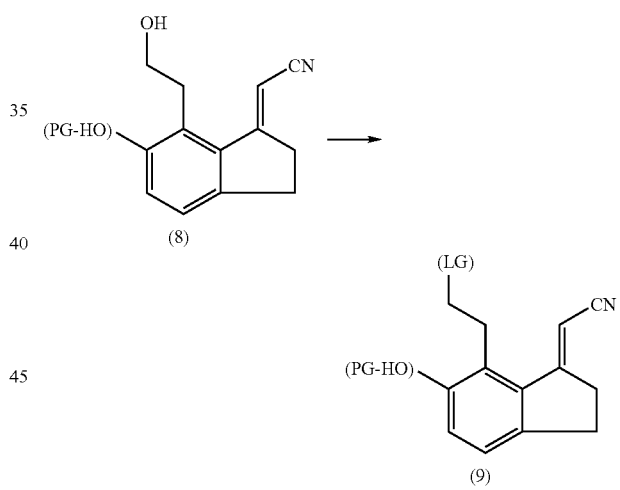

H) intramolecular cyclisation of the intermediate of formula (9) to obtain (1,6,7,8-tetrahydro-2H-indeno[5,4-b]furan-8-ylidene)acetonitrile of formula (10):

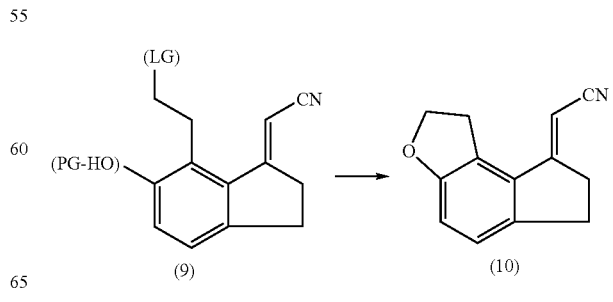

I) enantioselective reduction on the intermediate of formula (10) to obtain (1,6,7,8-tetrahydro-2H-indeno [5,4-b]furan-8-yl)acetonitrile of formula (XI):

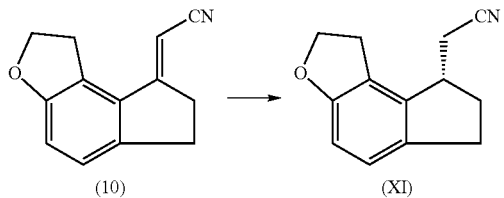

The intermediate (XI), a common product of the two synthesis pathways, can be made to react to obtain ramelteon according to one of the following two pathways:

α) hydrogenating the triple bond —C≡N in the presence of propionic anhydride to obtain ramelteon (I):

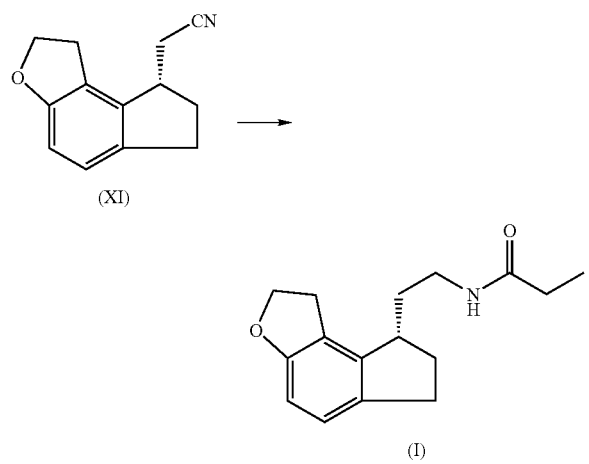

or

β¹) reducing the triple bond of the group —C≡N to —CH$_2$NH$_2$ to obtain the intermediate (XII); and β²) reacting the intermediate (XII) with propionic anhydride or propionyl chloride, to obtain ramelteon (I):

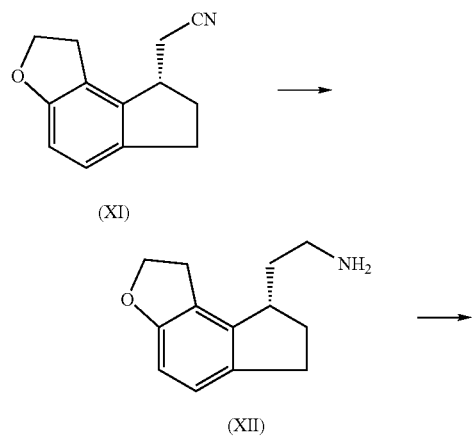

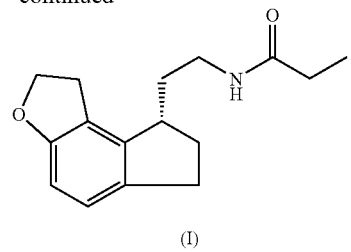

The intermediate (XII) can be salified, using organic acids such as oxalic acid, tartaric acid, malic acid, mandelic acid or inorganic acids such as hydrochloric or hydrobromic acid, and crystallised to obtain a first purification.

The ramelteon obtained is definitively purified by crystallisation using ordinary organic solvents such as ethyl acetate and isopropyl acetate, n-hexane, n-heptane, hexane mixture of isomers, heptane mixture of isomers, toluene, acetonitrile, methanol, ethanol, isopropanol, acetone, methyl ethyl ketone, methyl isobutyl ketone, methyl tert-butyl ether, diisopropyl ether or ethyl ether, pure or in a mixture.

The intermediates having general formula (V), (VI), (VII), (VIII), (IX), (X), (XI), (7), (8) and (9) constitute further objects of the invention.

With respect to the known processes, the process of the invention offers the advantages of providing ramelteon with high purity by means of simple purifications, for example by crystallisation, without having to resort to chromatographic purifications which are essentially not applicable to industrial production and, above all, of eliminating chiral hydrogenations at pressures of 90-100 bar.

BRIEF DESCRIPTION OF THE DRAWINGS

Characteristics and advantages of the present process will be illustrated in detail in the following description with reference to the figures (FIGS. 1A and 1B), which shows the HPLC analysis with chiral column of the ramelteon that can be obtained by means of the process described.

DETAILED DESCRIPTION

Figure 1A:
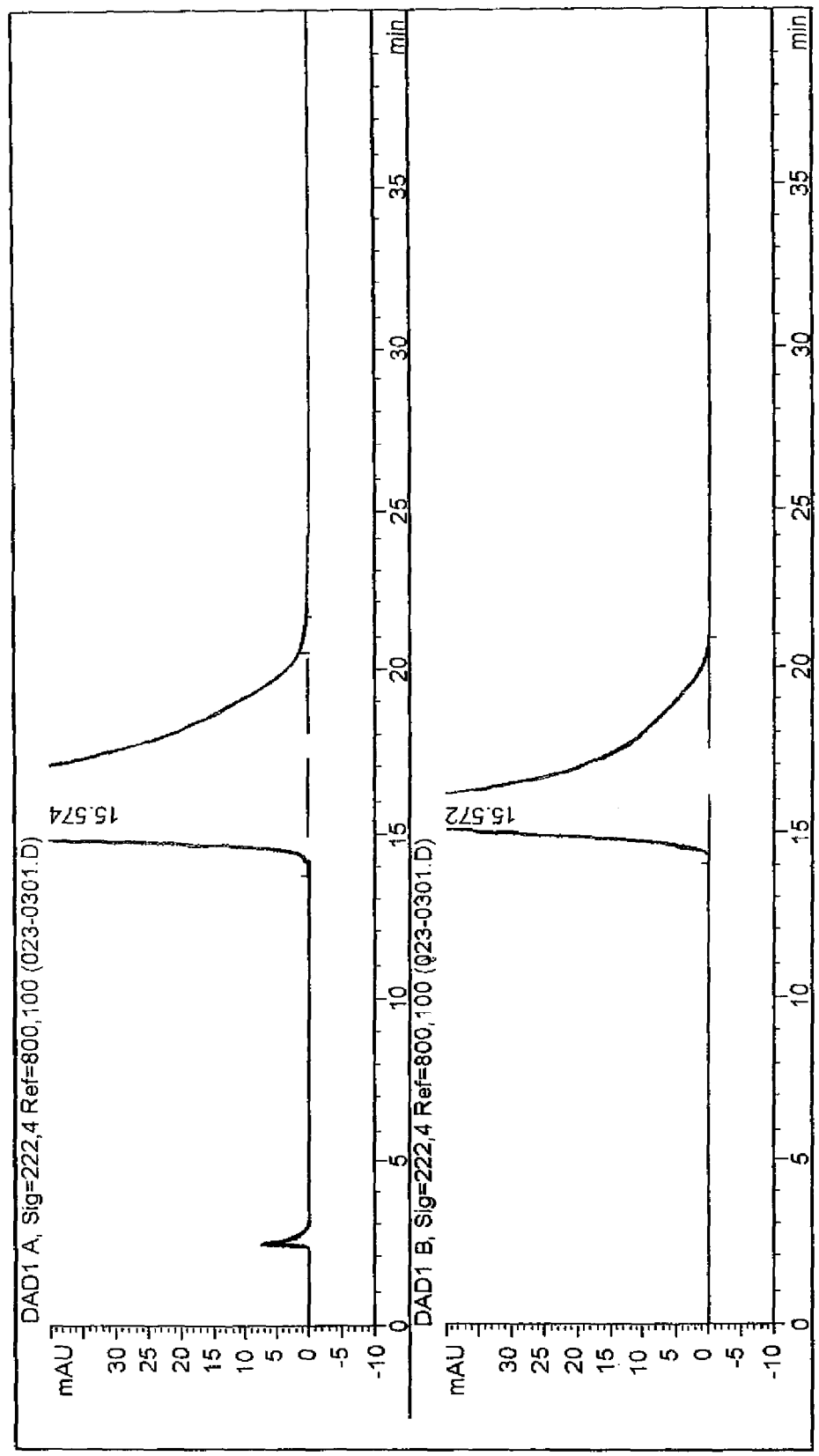

The starting product, 6-hydroxy-indanone, is a readily available commercial product.

Reaction a (preparation of the intermediate (III), 6-allyloxy-indan-1-one) can be easily performed by means of known methods, for example by reaction of the 6-hydroxy-indanone with allyl bromide in the presence of bases, as described in Magn. Reson. Chem., 2000, 38, 970-4. The reaction can be easily performed in acetone at reflux with allyl bromide slightly in excess with respect to the stoichiometric amount. The intermediate (III) is purified by crystallisation with n-heptane or a mixture of isomers of heptane or with cyclohexane.

Reaction b (preparation of the intermediate (IV), 7-allyl-6-hydroxy-indan-1-one) can be performed by thermal Claisen rearrangement of the intermediate (III) operating by melting without any added solvent, as described in Magn. Reson. Chem., 2000, 38, 970-4, or by operating in the presence of Dowtherm A (a liquid mixture consisting of 26.5% by weight of diphenyl and 73.5% by weight of diphenyl oxide produced by Dow Chemical Company and used for heat transfer). The reaction can be performed for a period of between 45 minutes and 80 hours at a temperature of between 140 and 250° C. The reaction is preferably performed in the presence of Dowtherm A, for no longer than 70 hours at a temperature below 210° C. The intermediate (IV) is easily purified from the non-reacted intermediate (III) by treatment with bases, extraction with water and subsequent acidification or by crystallisation with toluene. The by-product of rearrangement of the allylic group in position 5 of indane is produced in percentages below 4%.

Reaction c, protection of the phenolic hydroxyl to obtain an intermediate of general formula (V), can be performed with a protective group stable in a basic environment. The protections that give rise to the formation of an ether, for example 2-methoxypropene or a silyl ether, are useful for this purpose. Preferably compounds of silicon are used, including triisopropylsilyl chloride (TIPS)-Cl, trimethylsilyl chloride (TMS)-Cl, triphenylsilyl chloride (TPS)-Cl, t-butyldiphenylsilyl chloride (TBDPS)-Cl, texyldimethylsilyl chloride (TDS)-Cl, t-butyldimethylsilyl chloride (TBS)-Cl and similar, as described in "Greene's Protective Groups in Organic Synthesis" 4$^a$ Ed. Wiley, or in "Protecting groups" by P. J. Kocienski, ed. Thieme, in the presence of bases such as imidazole or dimethylaminopyridine (DMAP). Preferred compounds for the purpose are (TBDPS)-Cl and (TMS)-Cl. The reaction solvent is a solvent without hydroxylic groups, chosen for example from the group consisting of dimethylformamide (DMF), toluene, xylene, methylene chloride, ethyl ether, dimethoxyethane, tetrahydrofuran (THF), 2-methyl tetrahydrofuran, 3-methyl tetrahydrofuran and their mixtures; DMF is preferred. The reaction temperature can be between 0° C. and the boiling temperature of the solvent, preferably between 0 and 50° C., and even more preferably between 0 and 25° C. The reaction time is between 1 and 12 hours, preferably between 3 and 9 hours. The reaction product thus obtained can be easily purified from by-products and residues of non-reacted intermediate (IV) by crystallisation with heptane.

Reaction d, preparation of an intermediate of formula (VI), can be performed on the intermediate (V) with a dialkyl cyano methylphosphonate, for example diethyl cyano methylphosphonate, in a basic environment. The following can be used as a base: potassium t-butylate, sodium methylate, sodium hydroxide, potassium hydroxide, sodium hydride, stabilised sodium hydride, potassium hydride, sodium amide, lithiodiisopropylamide. Preferably sodium hydride is used at 60% dispersed on oil. The solvent can be one or a mixture of ethers such as ethyl ether, diisopropylether, tetrahydrofuran (THF), dioxane or dimethoxyethane; hydrocarbons, such as toluene, cyclohexane or heptane; amides, such as dimethylformamide and dimethylacetamide; or dimethylsulphoxide; preferably THF is used. The reaction temperature, between 0° C. and the boiling point of the solvent, is preferably comprised between 15 and 30° C.

The enantioselective reduction reactions e and I, for production of the intermediates of formula (VII) and (XI) starting from an intermediate of formula (VI) and an intermediate of formula (10) respectively, can be performed with "Josiphos" type reagents in the series (S)-(R) in the presence of a compound of copper (II), a silane and an alcohol in a hydrocarbon as solvent. The "Josiphos" reagents, characterised by a ferrocenic structure to which two phosphines are bound, are a family of catalysts suitable for enantioselective reductions. Of the Josiphos reagents that can be used, the ethanol adduct of (S)-1-[(R)-2-diphenylphosphino)ferrocenyl]ethyldicyclohexylphosphine, marketed as (S)-(R)-PPF-Pcy$_2$ (CAS no. 162291-02-3), is particularly efficient. The quantity of Josiphos that can be used in the reaction varies between a molar percentage of 0.1 and 6%, preferably between a molar percentage of 1 and 5% with respect to the reagents (VI) and (10).

The reaction temperature, which can vary from −5 to +20° C., is preferably maintained between 0 and 5° C. Of the silanes that can be used and are commercially available, including the polysilanes, diphenylsilane is preferred. Of the copper compounds (II) that can be used, copper (II) acetate is preferred. Of the alcohols that can be used, tert-butanol is preferred. The reaction solvents that can be used, inert in the reaction conditions, are for example heptane, hexane, cyclohexane or toluene, the latter being preferred.

The reaction is performed in an inert atmosphere without oxygen, preferably in a nitrogen atmosphere. The enantiomeric excess that can be obtained, always greater than 75%, using (S)-(R)-PPF-Pcy$_2$ is above 90%.

The reagents are added in three phases: 1) compound of copper (II)+Josiphos+silane+toluene; 2) reaction substrate+toluene; 3) alcohol+toluene.

Reactions f and E result in production of the intermediates of formula (VIII) and (7) starting from the intermediate (VII) and the intermediate (VI) respectively by oxidative demolition of a carbon atom. In the case of the intermediate (VI) said demolition is selective in relation to the double terminal bond, while the double bond conjugated with the function —C≡N is inert. Said reaction is performed by using 4-methylmorpholine-N-oxide with osmium tetroxide (OsO$_4$) in a catalytic quantity in an aqueous environment. 4-methylmorpholine-N-oxide can be used indifferently as a monohydrate or as an aqueous solution. Osmium tetroxide can be used as is or dissolved in tert-butanol or isopropanol. The reaction with OsO$_4$ is followed by the addition of sodium metaperiodate (NaIO$_4$) in water to complete the reaction. The intermediate diols of the oxidative demolition (having the formulas given below), obtained by treatment with OsO$_4$ and previous to the addition of metaperiodate, can be isolated from the reaction environment.

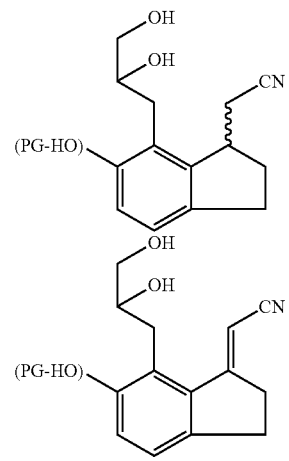

The reaction solvent is chosen from the common organic solvents which do not react in the reaction conditions and which are, also partially, miscible with water, for example methyl-tetrahydrofuran, methyltertbutylether, diisopropylether and, preferably, THF. The reaction temperature is comprised between 0 and 50° C., preferably between 15 and 30° C. In this case it is not necessary to work in an inert atmosphere; this working consition is however preferable for safety reasons.

The reactions g and F, which result in the production of intermediates of formula (IX) and (8) starting from the intermediate (VIII) and the intermediate (7) respectively, can be performed by reduction with a hydride such as lithium aluminium hydride (LiAlH$_4$), lithium borohydride (LiBH$_4$) or sodium borohydride (NaBH$_4$). The hydride can be used as a solid (powder, granules, flakes), as a solution in 2-methoxyethylether, tetraethylene glycol dimethyl ether, triethylene glycol dimethyl ether or, as regards NaBH$_4$, as an aqueous solution basified to pH>8 with sodium bicarbonate, sodium carbonate or NaOH. The reaction solvent is chosen from THF, methanol, ethanol, isopropanol, tertbutanol, ethyl ether, water or their mixtures; isopropanol is preferred. The quantity of hydride that can be used depends on the course of the reaction with extra additions of hydride until completion of the same. The reaction temperature is comprised between 0 and 50° C., preferably between 15 and 30° C. Also in this case, it is possible and advisable, although not necessary, to work in an inert atmosphere for safety reasons.

The reactions h and G result in the intermediates of formula (X) and (9), in which (LG) is a good leaving group in the following cyclisation reaction. The LG groups are preferably mesylate, —O—SO$_2$—CH$_3$, and tosylate, —O—SO$_2$—C$_6$H$_4$—CH$_3$; intermediates of type (X) and (9) containing these leaving groups can be prepared starting from the intermediate (IX) and the intermediate (8) respectively by reaction with mesyl chloride (CH$_3$SO$_2$Cl) or tosyl chloride (CH$_3$—C$_6$H$_4$—SO$_2$Cl) in pyridine. For completion of the reaction, between 2 and 8, preferably 5, moles of chloride are necessary per mole of reagent intermediate. The reaction temperature is comprised between 0 and 40° C., preferably between 15 and 30° C. The chloride can be added all at once at the beginning of the reaction, or in portions, monitoring the formation of the product by means of TLC.

The reactions i and H result in the intermediates of formula (XI) and (10) starting from the intermediate (X) and the intermediate (9) respectively by reaction with a salt obtained in its turn from reaction of hydrofluoric acid with an amine. For this purpose it is possible to use, for example, benzyltrimethylammonium fluoride hydrate, ammonium fluoride, pyridinium fluoride or tetrabutylammonium fluoride, in the form of pure salts, supported on silica gel, in aqueous solution or in hydrated form; use of the tetrabutylammonium fluoride in the form of trihydrate is preferred. The tetrabutylammonium fluoride trihydrate can be used in a molar amount between 5% and 200% with respect to the moles of the starting intermediate. To favour the reaction, KF can be added in a molar amount between 5% and 300% with respect to the moles of said intermediate. The reaction solvent is chosen from THF, ethyl ether, methyltertbutylether, methyltetrahydrofuran, methylene chloride, toluene, cyclohexane, ethyl acetate and isopropyl acetate, pure or in a mixture. The reaction can also be performed in biphase conditions. The reaction temperature is comprised between 0 and 40° C. The reaction is preferably performed in a THF-water biphase system at a temperature of between 10 and 30° C., using tetrabutylammonium fluoride trihydrate in the presence of KF, in molar amounts of between 10% and 20% and between 150% and 250% respectively with respect to the moles of the starting intermediate.

Lastly, ramelteon, having the formula (I) previously reported, can be produced directly by reduction of the intermediate (XI) in the presence of propionic anhydride or propionic acid, or by reduction of the intermediate (XI) to form a new intermediate (XII) and reaction of the latter with propionyl chloride, propionic anhydride or propionic acid.

Direct conversion of the intermediate (XI) to ramelteon, reaction α, can be performed by catalytic hydrogenation in the presence of propionic anhydride or propionic acid, using catalysts based on Pd, Rh, and Pt supported on inert substrates such as carbon or alumina, or Raney nickel, a product commercially available in aqueous suspension. If a noble metal is used on an inert support, the weight percentage of the metal with respect to the support is between 5% and 10%. The reaction occurs at a pressure of between 6 and 60 bar and at a temperature of between 20 and 120° C. The reaction solvent is chosen from the solvents that are non-hydrogenable in the reaction conditions such as THF, ethyl acetate, isopropyl acetate, DMF (dimethylformamide), DMA (dimethylacetamide), methyl-tetrahydrofuran, water, cyclohexane, toluene, methanol, ethanol or isopropanol, pure or in a mixture. The hydrogenation is preferably performed using Pt/C ESCAT 22 (a catalyst consisting of platinum on carbon produced by BASF SE) at a pressure of between 8 and 14 bar and a temperature of between 60 and 70° C. in THF. Propionic anhydride is used preferably in a number of moles twice the number of moles of reagent to be hydrogenated.

In the alternative preparation method, intermediate (XI) is first reduced by the reaction β$^1$ to form an amine (intermediate (XII)), which is then converted to ramelteon in the reaction β$^2$.

The conversion to ramelteon of intermediate (XII) can take place on the intermediate as is, i.e. the free amine, or on one of its salts with an acid, for example hydrochloride.

Reaction β$^1$ according to this preparation method can be performed in various ways:

hydrogenation of intermediate (XI) with Raney nickel; the hydrogenation can occur at a temperature of between 10 and 120° C. and at a pressure of between 1 and 60 bar in a solvent that is non-hydrogenable in the reaction conditions such as THF, ethyl acetate, isopropyl acetate, DMF, DMA, methyl-tetrahydrofuran, water, cyclohexane, toluene, methanol, ethanol and isopropanol, pure or in a mixture, possibly in the presence of ammonia. The reduction is preferably performed at a pressure of between 1 and 18 bar and at a temperature of between 10 and 40° C. in a THF-methanol mixture with the addition of ammonia;

reduction of the intermediate (XI) with Raney nickel in a mixture inert in the reaction conditions containing isopropanol in the presence of KOH without the addition of hydrogen; the reaction can occur at a temperature of between 30° C. and the reflux temperature of the reaction suspension. The reaction is preferably carried out using pure isopropanol as a solvent and operating at the reflux temperature of the reaction suspension. The quantity of KOH used is between 20 and 40%, preferably 30% by weight, with respect to the quantity of intermediate (XI) to be reduced;

reduction of the intermediate (XI) with lithium aluminium hydride in THF; the reaction is carried out with subsequent additions of the hydride until the reaction is complete (verified with TLC) at a temperature comprised between 0 and 40° C., preferably between 15 and 25° C., in an inert atmosphere. The quantity of hydride used is at least equal in weight to the quantity of intermediate (XI) to be reduced;

catalytic hydrogenation of the intermediate (XI) with catalysts based on Pd, Rh and Pt supported on inert substrates such as carbon and alumina in the presence of hydrogen; the weight percentage of the metal with respect to the support is between 5 and 10%. The reaction is performed at a hydrogen pressure comprised between 6 and 60 bar and at a temperature comprised between 20 and 120° C., in a solvent with the addition of ammonia or hydrochloric acid. The solvent is chosen from those that are non-hydrogenable in the reaction conditions such as THF, ethyl acetate, isopropyl acetate, DMF, DMA, methyl-tetrahydrofuran, water, cyclohexane, toluene, methanol, ethanol or isopropanol, pure or mixed. The reaction is preferably performed using Pt/C ESCAT 22 and operating at a pressure of between 8 and 14 bar and a temperature of between 60 and 70° C. in a THF-methanol-ammonia mixture.

The intermediate (XII), obtained according to any one of the four possible methods illustrated above, is then converted to ramelteon by simple reaction ($\beta^2$) with a reagent chosen from propionyl chloride, propionic acid or propionic anhydride in the presence of a base. Propionyl chloride is preferably used with triethylamine (TEA) for reaction in organic solvent or propionic anhydride for reactions in the presence of water as part of the solvent mixture.

If the intermediate (XII) is used as the salt of an acid, easily obtainable with the common methods of salification of an amine, the quantity of base to be used will be consequently increased.

The invention will be further illustrated by the following examples. In the description of the examples, the term (TLC) after a process phase indicates control of the advancement degree or verification of the end of a reaction by thin layer chromatography.

EXAMPLE 1

This example refers to reaction a of the process of the invention.

20 kg of 6-hydroxy-indanone are suspended in 120 l of acetone, and 29.9 kg of potassium carbonate and 19.7 kg of allyl bromide are added. The reaction mixture is heated to reflux and checked after 15 h (TLC). It is cooled to 20-25° C. and filtered, washing the filtered solid with 40 l of acetone. The filtered solution is concentrated to dryness at reduced pressure. The oil obtained is recovered with 25 l of heptane and re-concentrated to dryness obtaining a solid (25.9 kg). The thus obtained solid is dissolved at 60° C. in 125 l of heptane, and is then cooled to 0° C. for at least one hour. It is filtered and washed with 25 l of cold heptane. 22.3 kg of intermediate (III) are obtained in a pale yellow solid form of quality suitable for continuation of the synthesis.

An $^1$H-NMR (500 MHz, CDCl$_3$) spectroscopic analysis is performed on part of the product thus obtained, purified by chromatography for analytical purposes (silica gel, heptane 8-ethyl acetate 2), obtaining the following result:

2.74 ppm, t J=6 Hz, 2H, 3.10 ppm, t, J=6 HZ, 2H, 4.60 ppm, broad d, J=5 Hz, 2H, 5.32 ppm, dd, J=10 Hz, 1H, 5.45 ppm, broad dd, J=16 Hz, 1H, 6.02-6.13 ppm, m, 1H; 7.20-7.27 ppm, m, 2H, 7.40 ppm, d, J=8 Hz, 1H.

EXAMPLE 2

This example refers to reaction b of the process of the invention.

20 kg of the intermediate of formula (III) prepared as described in example 1 are suspended in 50 l of Dowtherm A under nitrogen flow. In an inert atmosphere, it is heated to approximately 200° C. for approximately 5 hours. Upon completion of the reaction (TLC) a clear red-brown solution is obtained, without the formation of black pitch. The reaction mixture is cooled slowly to 25° C. (a partial precipitation is observed). 100 l (5 volumes) of cyclohexane are added and it is cooled to between 0 and 5° C. for one hour. It is filtered by washing with cyclohexane and dried at reduced pressure and T=45° C. for at least 12 hours. 16.8 kg of yellow solid are obtained which is refluxed in 80 l of toluene in the presence of decolouring carbon. The suspension is filtered, washing it with hot toluene. Part of the solvent is distilled at reduced pressure until the beginning of crystallisation. It is cooled at room temperature and then to between 0 and 5° C. for at least one hour.

The filtered solid is washed with cold toluene and dried at reduced pressure at T=45° C. for at least 12 hours. 15.3 kg of intermediate (IV) are obtained in the form of an almost white solid of quality suitable for continuation of the synthesis.

$^1$H-NMR and mass spectroscopic analyses are performed on part of the product thus obtained, purified by chromatography for analytical purposes (silica gel, 7 parts in volume of heptane—3 parts in volume of ethyl acetate), obtaining the following results:

Electron impact mass: [M$^+$]=188

$^1$H-NMR (500 MHz, CDCl$_3$): δ (ppm)

2.72 ppm, t, J=6 Hz, 2H, 3.03 ppm, t, J=6 Hz, 2H, 4.03 ppm, d, J=6 Hz, 2H, 5.13-5.20, Σd, 2H, 5.60 ppm, s, 1H, 5.98-6.10 ppm, m, 1H, 7.13 ppm, d, J=8 Hz, 1H, 7.25, d, J=8 Hz, 1H.

EXAMPLE 3

This example refers to reaction c of the process of the invention.

20 kg of intermediate (IV), prepared as described in the preceding example, are dissolved in 200 l of DMF. 25.2 kg of imidazole are added and it is cooled to a temperature between 0 and 5° C. 38 kg of tert-butydiphenylchlorosilane are added dropwise and it is left under agitation at 20° C., monitoring the reaction (TLC). Upon completion of the reaction, cooling to 0-5° C. is performed, 400 l of water are added to the reaction mixture and it is agitated for a few minutes before filtering the solid formed. The solid is dissolved with 300 l of toluene, the toluene solution is washed with water before distilling the toluene at reduced pressure. The oily residue is recovered with 100 l of heptane which are distilled at reduced pressure. The solid is recovered again with 340 l of heptane and dissolved at 60° C. It is cooled to 0-5° C. for at least one hour. Filtering is performed, washing with cold heptane. It is dried at reduced pressure and T=45° C. for at least 8 hours. 34 kg of intermediate (V) are obtained in the form of a white solid of suitable quality for continuation of the synthesis.

A sample of the product thus obtained, after purification by crystallisation with isopropyl ether for analytical purposes, undergoes $^1$H-NMR and mass analysis obtaining the following result:

Electron impact mass: [M$^+$]=426, [M$^+$]=426−C$_4$H$_9$=369

$^1$H-NMR (500 MHz, CDCl$_3$): δ (ppm)

1.15 ppm, s, 9H, 2.70 ppm, t, J=6 Hz, 2H, 2.94, t, J=6 Hz, 2H, 4.13 ppm, broad d, J=6 Hz, 2H, 5.00-5.18 ppm, Σd, 2H, 6.10-6.20 ppm, m, 1H, 6.65 ppm, d, J=8 Hz, 1H, 6.85 ppm, d, J=8 Hz, 1H; 7.38-7.50 ppm, m, 6H, 7.75 ppm, broad d, J=6 Hz, 4H.

EXAMPLE 4

This example refers to reaction d) of the process of the invention.

3.0 kg of sodium hydride at 60% are agitated with 70 kg of THF in an inert atmosphere, maintaining the temperature at 20±5° C. 14.4 kg of diethyl(cyanomethyl)phosphonate are added maintaining the temperature at 20±5° C. with suitable cooling, given the slight exothermicity of the reaction. It is maintained at 20±5° C. for 45 minutes. The reaction mixture becomes a solution.

13.9 kg of intermediate (V), prepared as described in the preceding example, are dissolved in 35 kg of THF at a temperature of 20±5° C. The solution of intermediate (V) is added to the solution of phosphonate, maintaining the temperature at 20±5° C. with suitable cooling. The reaction mixture is kept under agitation at 20±5° C. for 5 h. Upon completion of the reaction (TLC), the reaction mixture is quenched in a solution consisting of 118 liters of water and 2.4 liters of glacial acetic acid pre-cooled to 5±5° C.; during the addition, precipitation of the product occurs. The system is kept under agitation at 5±5° C. for 30 minutes, after which the solid is filtered and washed with 25 liters of water. The wet solid is then recovered in 85 l of water, agitated at 20±5° C. for 30 minutes and re-filtered, washing the solid with 30 l of water. The solid is dried under a vacuum at 45±5° C. until the weight is constant. 11.5 kg of raw intermediate (VI) are obtained; the solid is dissolved at reflux in 25 kg of toluene, treated with carbon and filtered. The solution is concentrated distilling part of the solvent, obtaining crystallisation of the product. 16 kg of heptane are added and it is cooled to 0±5° C. for at least one hour to complete the crystallisation. The solid is filtered, washing it with heptane, and dried at reduced pressure and T=45° C. for at least 8 hours. 9.4 kg of intermediate (VI) are obtained in the form of a white solid of quality suitable for continuation of the synthesis.

A sample of intermediate (VI) thus obtained, after chromatographic purification for analytical purposes, undergoes $^1$H-NMR and mass analysis obtaining the following result:

Electron impact mass: [M$^+$]=449, [M$^+$]=449–C$_4$H$_9$=392, [M$^+$]=449–C$_4$H$_9$–C$_6$H$_6$=314

$^1$H-NMR (500 MHz, CDCl$_3$): δ (ppm)

1.10 ppm, s, 9H, 2.94 ppm, m, 2H, 3.12, m, 2H, 3.81 ppm, m, 2H, 4.96 ppm, broad d, J=16 Hz, 1H, 5.20 ppm, broad d, J=12 Hz, 1H, 5.73 ppm, t, J=1 Hz, 1H, 6.06-6.15 ppm, m, 1H; 6.50 ppm, d, J=8 Hz, 1H, 6.81 ppm, d, J=8 Hz, 1H, 7.40 ppm, t, J=6 Hz, 4H, 7.46 ppm, t, J=6 Hz, 2H, 7.72 ppm, d, J=6 Hz, 4H.

EXAMPLE 5

This example refers to reaction e of the process of the invention.

All the phases of this reaction take place in an inert atmosphere (nitrogen). A mixture of 20 l of toluene, 163 g of Josiphos, 46 g of copper (II) acetate is cooled to 0-5° C. 2.7 kg of diphenylsilane are added and it is kept under agitation at 0-5° C. for approximately 30 minutes. A suspension of 20 l of toluene and 3.8 kg of intermediate (VI), maintained at T=10° C., is prepared separately. This suspension is transferred to the mixture containing Josiphos, maintaining the system at a temperature between 0 and 5° C. A solution of 2.2 kg of tertbutanol in 9.7 l of toluene is prepared separately and cooled to T=10° C. The solution of tertbutanol is transferred to the suspension of intermediate (VI) and Josiphos, maintaining the system at a temperature between 0 and 5° C. It is agitated until the end of the reaction (TLC); as the reaction progresses, the initial suspension becomes a solution. A solution of 6.4 kg of NaOH at 30% in water and 14 l of water is prepared separately and cooled to T=10° C. Upon completion of the reaction (TLC), the basic solution is transferred to the reaction solution maintaining the temperature between 0 and 5° C.; a biphasic system is obtained. Upon completion of the addition, the biphasic system is brought back to T=20° C. and the phases are separated. The aqueous phase is re-extracted with 30 l of toluene and the organic phases are collected and washed with water until neutral pH is obtained. 1 kg of dicalite is added to the organic phase and the suspension is filtered. The solvent is eliminated from the organic phase, distilling at reduced pressure and T=40-50° C. The oily residue obtained is crystallised with the addition of 76 l of heptane at T=20-25° C. It is cooled for at least two hours at T=0-5° C. and the solid is filtered. It is dried at reduced pressure at a temperature of between 45 and 50° C. until the weight is constant. 2.91 kg of intermediate (VII) are obtained of quality suitable for continuation of the synthesis.

A sample of the product thus obtained, after chromatographic purification for analytical purposes, undergoes $^1$H-NMR and mass analysis obtaining the following result:

Electron impact mass: [M$^+$]=451, [M$^+$]=451–C$_4$H$_9$=394, [M$^+$]=451–C$_4$H$_9$–C$_6$H$_6$=316

$^1$H-NMR (500 MHz, CDCl$_3$): δ (ppm)

1.10 ppm, s, 9H; 2.15 ppm, m, 1H; 2.30-2.42 m, 2H, 2.65-2.80 ppm, m, 2H, 2.95-3.05 ppm, m, 1H, 3.48-3.70 ppm, m, 3H, 5.00 ppm, broad d, J=18 Hz, 1H, 5.12 ppm, broad d, J=10 Hz, 1H, 6.10-6.22 ppm, m, 1H, 6.35 ppm, d, J=8 Hz, 1H, 6.68 ppm, d, J=8 Hz, 1H, 7.35-7.50 ppm, m, 6H, 7.68-7.78 ppm, dd, J=6 Hz, 22 Hz, 4H.

Example 6

This example refers to reactions f and g of the process of the invention. In this example the intermediate (VIII) is not isolated, obtaining the intermediate (IX) directly.

2.75 kg of the product of formula (VII), obtained as described above in example 5, are dissolved in 46 l of THF. 7 l of water and 46.5 g of osmium tetroxide dissolved in 1.9 l of tert-butanol are added to the solution, maintained at T between 20 and 25° C. Lastly 3.3 kg of N-methylmorpholine-N-oxide in aqueous solution at 50% at the same temperature are added and it is kept under agitation until the end of the reaction (TLC). A suspension of 3.9 kg of NaIO$_4$ in 39 l of water is prepared separately. Upon completion of the reaction, the suspension of NaIO$_4$ is added to the mixture with OsO$_4$ and agitated, at T=20-25° C., until the end of the reaction (TLC). Upon completion of the reaction, 46 l of isopropyl acetate are added to the reaction mixture, the suspension is filtered and the phases are separated. The aqueous phase is re-extracted with isopropyl acetate, the organic phases are collected and washed with 150 l of a solution of sodium sulphite at 2.5% in water and with 100 l of a solution of NaCl at 5% in water. The solvent is eliminated from the organic phase by distillation at reduced pressure and T=40-50° C. until an oily residue is obtained, which is recovered with 28 l of isopropanol, heated to T=40-50° C. and then cooled to T between 0 and 5° C. (with partial precipitation). 230 g of NaBH$_4$ are added and it is kept under agitation at T=20-25° C. until the end of the reaction (TLC). Upon completion of the reaction it is cooled to T between 0 and 5° C. and 460 g of acetic acid at 80% in water followed by 28 l of water at T=20-25° C. are added. After a few minutes of agitation (after all the gases have developed) the solvent is distilled at reduced pressure and T=45-50° C. until a residual volume of approximately 35 l is obtained. It is brought back to T=20-25° C. and extracted with 56 l of isopropyl acetate. The aqueous phase is re-extracted with 30 l of isopropyl acetate, then the organic phases are collected and washed with 110 l of water. The organic phase is recovered with 300 g of decolouring carbon and with 1 kg of dicalite. The suspension is filtered and the solvent is eliminated from the organic phase, distilling at reduced pressure and T=40-50° C. The oily residue obtained (2.35 kg) is the intermediate (IX) of quality suitable for continuation of the synthesis.

The intermediate (IX), after chromatographic purification for analytical purposes, undergoes $^1$H-NMR and mass analysis obtaining the following result:

Electron impact mass: $[M^+]=455$, $[M^+]=455-C_4H_9-C_6H_6=320$ $^1$H-NMR (500 MHz, CDCl$_3$): δ (ppm)

1.12 ppm, s, 9H, 1.58 ppm, broad s, >1H, 2.12-2.20 ppm, dd, J=6 Hz, J=12 Hz, 1H, 2.30-2.40 ppm, m, 1H, 2.42-2.50 ppm, dd, J=10 Hz, J=16 Hz, 1H, 2.70-2.82 ppm, m, 2H, 2.95-3.08 ppm, m, 2H, 3.10-3.18 ppm, m, 1H, 3.65-3.70, m, 1H, 3.98-4.10 ppm, m, 2H, 6.36 ppm, d, J=8 HZ, 1H, 6.68 ppm, d, J=8 Hz, 1H, 7.36-7.49 ppm, m, 6H, 7.68-7.76 ppm, dd, J=8, J=16 Hz, 4H.

EXAMPLE 7

This example refers to reaction h of the process of the invention.

2.35 kg of the product of formula (IX) obtained as described in example 6 are dissolved in 4.9 l of pyridine heating to T between 40 and 45° C. 1 kg of methanesulphonyl chloride is slowly added to this solution, cooled to 0±5° C. The temperature is brought to 20±5° C. and it is left under agitation for approximately 2 hours, monitoring the progress of the reaction (TLC). In a separate reactor, a biphasic solution with sodium bicarbonate 2.2 kg, water 24 l, isopropyl acetate 21 kg is prepared and cooled to 10±5° C. At the end of the reaction, the reaction mixture is loaded on the basic mixture and agitated, maintaining a temperature of 10±5° C. After all the gases have developed, the temperature is brought back to 20±5° C. and the phases are separated. The aqueous phase is re-extracted with 10 kg of isopropyl acetate, the organic phases are collected and washed twice with an acid solution (17 l of water+1.8 kg of concentrated hydrochloric acid). The organic phase is washed with a solution of 3.2 kg of NaCl in 18 l of water. The organic phase is concentrated to dryness distilling the solvent at a reduced pressure and T 45±5° C. 3 kg of intermediate (X) are obtained in the form of an oily residue of quality suitable for continuation of the synthesis (TLC).

A sample of the product thus obtained, after chromatographic purification for analytical purposes, undergoes $^1$H-NMR and mass analysis obtaining the following result:

Electron impact mass: $[M^+]=533$, $[M^+]-C_4H_9-C_6H_6-CN=372$ $^1$H-NMR (500 MHz, CDCl$_3$): δ (ppm)

1.13 ppm, s, 9H; 2.13-2.19 ppm, dd, J=6 Hz, 1H, 2.30-2.40 ppm, m, 1H, 2.48-2.56 ppm, dd, J=8 Hz, J=16 Hz, 1H; 2.63-2.78 ppm Σdd, 2H; 2.86 ppm, s, 3H, 2.98-3.06 ppm, m, 1H, 3.15-3.22 ppm, m, 1H, 3.31-3.38 ppm, m, 1H, 3.63-3.69 ppm, m, 1H, 4.50-4.63 ppm, m, 2H, 6.40 ppm, d, J=8 HZ, 1H, 6.72 ppm, d, J=8 Hz, 1H, 7.38-7.50 ppm, m, 6H, 7.68-7.75 ppm, m, 4H.

EXAMPLE 8

This example refers to reaction i of the process of the invention.

The product of formula (X) obtained as described in example 7 is dissolved in 22 kg of THF at room temperature. 2.8 kg of tetrabutylammonium fluoride trihydrate are added to the solution ensuring that the temperature does not exceed 30° C. (slight exothermia). It is kept under agitation for at least one hour at T=25±5° C. monitoring the progress of the reaction (TLC).

In a separate reactor a solution of 9 kg of NaCl in 45 l of water is prepared. At the end of the reaction the solution of NaCl is poured onto the reaction solution regulating the temperature so that it does not exceed 30° C. It is agitated for a few minutes and then re-extracted twice with 18 kg of isopropyl acetate. The collected organic phases are washed twice with 30 kg of water. The organic phase is concentrated to dryness distilling the solvent at a reduced pressure and T=45±5° C. 2.40 kg of oily residue are obtained which is purified by chromatography on 40 kg of silica gel (heptane: ethyl acetate 85:15). After elimination of the solvent at reduced pressure and T=45±5° C., 934 g of intermediate (XI) is obtained which is refluxed in 2.8 l of methanol in the presence of decolouring carbon. The suspension is hot filtered. Part of the solvent is distilled at reduced pressure until a residual volume of approximately 2.4 l is obtained. It is cooled to 0<T<5° C. for approximately 2 hours before filtering the solid. The product is dried at T=45° C. and at reduced pressure for approximately 12 hours. 577 g of intermediate (XI) are obtained of quality suitable for continuation of the synthesis. A sample of the product thus obtained, after further chromatographic purification for analytical purposes, undergoes $^1$H-NMR and mass analysis obtaining the following result:

Electronic impact mass: $[M^+]=199$; $[M^+]-CH_2CN=159$ $^1$H-NMR (500 MHz, CDCl$_3$): δ (ppm)

1.98-2.08 ppm, m, 1H, 2.40-2.50 ppm, m, 1H, 2.52-2.59 ppm, dd, J=8 Hz, J=15 Hz, 1H, 2.66-2.75 ppm, dd, J=6 Hz, J=15 Hz, 1H, 2.81-2.88 ppm, m, 1H, 2.96-3.04 ppm, m, 1H; 3.13-3.22 ppm, m, 1H, 3.28-3.36 ppm, 1H, m; 3.48-3.56 ppm, m, 1H, 4.52-4.69 ppm, m, 2H, 6.69 ppm, d, J=8 Hz, 1H, 7.02 ppm, d, J=8 Hz, 1H.

EXAMPLE 9

This example refers to reaction a of the process of the invention (preparation of ramelteon).

470 g of product of formula (XI), obtained as described in Example 8, are dissolved in 84 kg of THF. 615 g of propionic anhydride and 150 g of Pt/C Escat 22 (Pt at 5% on carbon) are added to the solution. The suspension is brought to T=65±5° C. and hydrogenated at P=8/9 bar. After 4 h the progress of the reaction is checked (TLC), it is filtered and a further 50 g of Pt/C Escat 22 are loaded. The suspension is brought to T=65±5° C. and hydrogenated at P=8/9 bar, checking the progress of the reaction (TLC). At the end of the reaction, the catalyst is filtered and the solvent is eliminated at reduced pressure. The residue is recovered with 11 kg of isopropyl acetate. The organic phase is washed with a basic aqueous solution (900 g of NaHCO$_3$ in 10 l of water), with an aqueous solution of NaCl (500 g of NaCl in 10 l of water) and then with water until neutral pH is reached. The solvent is distilled at reduced pressure and T=55±5° C. The residue obtained, which tends to crystallise spontaneously, is crystallised with heptane and ethyl acetate. 380 g of ramelteon are obtained, the analytical characteristics of which match the data reported in literature.

This product, analysed with chiral HPLC (Ceramospher Chiral RU-1) shows an e.e. of 100%.

EXAMPLE 10

This example refers to reaction a of the process of the invention (preparation of ramelteon).

20 g of product of formula (XI) are dissolved in 1.8 kg of THF. 26 g of propionic anhydride and 5 g of Pt/C Escat 22 are added to the solution. The suspension is brought to T=65±5° C. and hydrogenated at P=10/12 bar. After 4 h the progress of the reaction is checked (TLC), it is filtered and a further 2.5 g of Pt/C Escat 22 are loaded. The suspension is brought to T=65±5° C. and hydrogenated at P=10/12 bar, checking the progress of the reaction (TLC). At the end of the reaction, the catalyst is filtered and the solvent is eliminated at reduced pressure. The residue is recovered with 1 l of isopropyl acetate. The organic phase is washed with a basic aqueous solution (10 g of $NaHCO_3$ in 1 l of water), with aqueous solution of NaCl (10 g of NaCl in 1 l of water) and lastly with water until neutral pH is reached. The solvent is distilled at reduced pressure and T=55±5° C. The residue obtained, which tends to crystallise spontaneously, is crystallised with heptane and ethyl acetate. 16.7 g of ramelteon are obtained, the characteristics of which match the data reported in literature.

EXAMPLE 11

This example refers to reaction E of the process of the invention.

The entire process is performed in an inert atmosphere (nitrogen). 100 g of intermediate (VI), obtained as described in example 4, are dissolved at room temperature in 1.7 l of THF. 170 ml of water, 84 ml of solution at 2.5% of $OsO_4$ in tert-butanol and 60 g of 4-methylmorpholine-N-oxide monohydrate are added. It is kept under agitation at T=20±5° C. checking the progress of the reaction (TLC). At the end of the reaction, 1 l of aqueous solution of NaCl at 5% and 1.7 l of isopropyl acetate are added to the reaction mixture. The phases are separated and the aqueous phase is re-extracted with 700 ml of isopropyl acetate. The collected organic phases, after further washing with 1 l of aqueous solution of NaCl, are concentrated to dryness at reduced pressure and T 40±5° C. 152 g of residue are obtained which, purified by chromatography on silica gel (heptane:ethyl acetate 3:1) provide 96 g of intermediate diol as a white solid.

A sample of the product thus obtained undergoes $^1$H-NMR and mass analysis obtaining the following result:

Electron impact mass: [M$^+$]=483

$^1$H-NMR (500 MHz, CDCl$_3$): δ (ppm)

1.13 ppm, s, 9H, 1.6 ppm, s, 1H, 2.03 ppm broad s, 1H, 2.45 ppm, d, J=4 Hz, 1H, 2.92 ppm, m, 2H, 3.05-3.35 ppm, m, 3H, 3.72 ppm, m, 1H, 3.85 ppm, m, 1H, 4.18 ppm, m, 1H, 6.08 ppm, t, J=2 Hz, 1H, 6.55 ppm, d, J=8 Hz, 1H, 6.79 ppm, d, J=8 Hz, 1H, 7.37-7.50 ppm, m, 6H, 7.67-7.76 ppm, m, 4H;

38 g of intermediate diol are dissolved in 680 ml of THF at room temperature. 56 g of $NaIO_4$ in 56 ml of water are added to the solution and agitated, maintaining a temperature<35° C. At the end of the reaction (TLC) it is recovered with 700 ml of isopropyl acetate, filtered on dicalite and the organic phase is separated. The aqueous phase is re-extracted with 800 ml of isopropyl acetate and the collected organic phases are washed with a reducing solution (1.5 l of aqueous solution at 2.5% of sodium sulphite) and with saline solution (1.5 l of aqueous solution at 5% of sodium chloride). The solvent is eliminated at reduced pressure and T=40±5° C. 36 g of intermediate (7) are obtained in the form of a slightly yellow solid of quality suitable for continuation of the synthesis.

A sample of the product thus obtained undergoes $^1$H-NMR and mass analysis obtaining the following result:

Electron impact mass: [M$^+$]=451

$^1$H-NMR (500 MHz, CDCl$_3$): δ (ppm)

1.10 ppm, s, 9H, 2.95 ppm, t, J=6 Hz, 2H, 3.14 m, 2H, 4.18 ppm, d, 2H, 5.66 ppm, t, 1H, 6.58 ppm, d, J=8 Hz, 1H, 6.86 ppm, d, J=8 Hz, 1H, 7.42 ppm, t, J=8 Hz, 4H, 7.48 ppm, m, 2H, 7.72 ppm, broad d, J=6 Hz, 4H, 9.85, t, 1H FT-IR (Kbr): band at 1716 cm$^{-1}$.

EXAMPLE 12

This example refers to reaction E of the process of the invention.

The entire process is performed in an inert atmosphere (nitrogen). 180 g of intermediate (VI), obtained as described in example 4, are dissolved at room temperature in 3 l of THF. 540 ml of water, 150 ml of solution at 2.5% of $OsO_4$ in tert-butanol and 108 g of 4-methylmorpholine-N-oxide monohydrate are added. It is kept under agitation at T=20±5° C. checking the progress of the reaction (TLC). At the end of the reaction, 3 l of isopropyl acetate and 1800 ml of solution of NaCl at 5% are added to the reaction mixture, then the phases are separated. The aqueous phase is extracted with 1.3 l of isopropyl acetate. The collected organic phases are washed with 2.5 l of solution of sodium sulphite at 3.5% and with 2.5 l of solution of NaCl at 5%.

The organic phase is concentrated to dryness at reduced pressure, obtaining 230 g of yellow oil (intermediate diol) which is used as is without further purifications. It is dissolved in 3.0 l of THF, heating to 45° C., and the solution is then cooled to 20° C. A suspension of 390 g of $NaIO_4$ in 4 l of water is prepared and added to the solution with the product; it is agitated, keeping the temperature at <40° C. At the end of the reaction (TLC) it is recovered with 2.7 l of isopropyl acetate, filtered on dicalite and the organic phase is separated. The aqueous phase is re-extracted with 1.8 l of isopropyl acetate. The collected organic phases are washed with reducing solution (1.8 l of aqueous solution at 3.5% of sodium sulphite) and with saline solution (1.8 l of aqueous solution at 5% of sodium chloride). The solvent is eliminated at reduced pressure and T=40±5° C. 211 g of solid product are obtained which, purified by chromatography on silica gel (heptane: ethyl acetate 9:1), provide 145 g of intermediate (7) in the form of a slightly yellow solid with analytical characteristics comparable to those of the product of example 11.

EXAMPLE 13

This example refers to reaction E of the process of the invention.

The entire process is performed in an inert atmosphere (nitrogen). 20 g of intermediate (VI), obtained as described in example 4, are dissolved at room temperature in 340 ml of THF. 60 ml of water, 16.7 ml of solution at 2.5% of $OsO_4$ in tert-butanol and 12.1 g of 4-methylmorpholine-N-oxide monohydrate are added. It is kept under agitation at T=20±5° C. checking the progress of the reaction (TLC). At the end of the reaction, 340 ml of isopropyl acetate and 200 ml of solution of NaCl at 5% are added to the reaction mixture and the phases are then separated. The aqueous phase is extracted with 140 ml of isopropyl acetate. The collected organic phases are washed with 280 ml of solution of sodium sulphite at 3.5% and with 280 ml of solution of NaCl at 5%.

The organic phase is concentrated to dryness at reduced pressure, obtaining 26 g of yellow oil (intermediate dial) which is dissolved in 340 ml of THF, heating to 45° C.; the solution is then cooled to 20° C.

A suspension of 43 g of $NaIO_4$ in 430 ml of water is prepared, added to the solution with the intermediate and agitated, keeping the temperature at <40° C. At the end of the reaction (TLC) everything is recovered with 300 ml of isopropyl acetate, filtered on dicalite and the organic phase is separated and washed with water. The aqueous phase is re-extracted with 200 ml of isoproyl acetate. The collected organic phases are washed with reducing solution (sodium sulphite in water) and with saline solution (sodium chloride in water). The solvent is eliminated at reduced pressure and T=40±5° C. 23 g of raw intermediate (7) are obtained.

The intermediate (7) is agitated with 100 ml of isopropanol at 60° C. for 30 minutes, cooled to 0° C. for one hour and filtered. After washing with isopropanol and drying, 18.3 g of intermediate (7) of quality suitable for continuation of the synthesis are obtained.

EXAMPLE 14

This example refers to reaction F of the process of the invention.

120 g of intermediate (7), obtained as described above, are dissolved in 1.2 l of isopropanol and treated with 10 g of NaBH$_4$. The reaction temperature is maintained below 15° C. during addition of the reducing agent. It is then kept under vigorous agitation at room temperature until the end of the reaction (TLC). At the end of the reaction, it is recovered with 16 ml of glacial acetic acid and 1.2 l of cold water, and agitated for approximately one hour maintaining T<10° C.

The isopropanol is distilled at reduced pressure, then the aqueous phase is extracted twice with 1 l of isopropyl acetate. The collected organic phases are washed with water. Having eliminated the solvent at reduced pressure and T=40±5° C., 104 g of intermediate (8) are obtained of quality suitable for continuation of the synthesis.

The intermediate (8), after chromatographic purification for analytical purposes, undergoes $^1$H-NMR and mass analysis obtaining the following result:

Electron impact mass: [M$^+$]=453–C$_4$H$_9$=396
$^1$H-NMR (500 MHz, CDCl$_3$): δ (ppm)
1.15 ppm, s, 9H, 1.75 ppm, broad s, >1H, 2.92 ppm, t, J=6 Hz, 2H,
3.15 ppm, m, 2H, 3.37 ppm, t, J=6 Hz, 2H, 4.0 ppm, t, J=6 Hz, 2H, 6.0 ppm, m, 1H, 6.55 ppm, d, J=8 Hz 1H, 6.80 ppm, d, J=8 Hz 1H;
7.40 ppm, broad t, J=6 Hz, 4H, 7.46 ppm, broad t, J=6 Hz, 2H, 7.75 ppm, broad d, J=6 Hz, 4H.

EXAMPLE 15

This example refers to reaction G of the process of the invention.

96 g of intermediate (8) obtained as described in example 14 are dissolved in 190 ml of pyridine, heating to a temperature between 40 and 45° C. 50 ml of methanesulphonyl chloride are added slowly to the above solution, cooled to approximately 10° C. It is left under agitation at 20±5° C. for approximately 2 hours checking the progress of the reaction (TLC). At the end of the reaction 2 l of isopropyl acetate and 1.8 l of aqueous solution saturated with sodium bicarbonate are loaded in the reaction mixture. It is agitated for approximately 30 minutes maintaining the temperature at approximately 20° C. The phases are separated and the aqueous phase is re-extracted three times with 0.6 l of isopropyl acetate. The organic phases are collected and washed with 1 l of acid aqueous solution (HCl 1 M) twice and three times with 1 l of aqueous solution saturated with NaCl. The organic phase is concentrated to dryness distilling the solvent at reduced pressure and T=45±5° C. 103 g of intermediate (9) are obtained in the form of a solid residue of quality suitable for continuation of the synthesis (TLC).

A sample of the product thus obtained, after chromatographic purification for analytical purposes, undergoes $^1$H-NMR analysis obtaining the following result:

$^1$H-NMR (500 MHz, CDCl$_3$): δ (ppm)
1.15 ppm, s, 9H, 2.92 ppm, t, J=6 Hz, 2H; 2.97 ppm, s, 3H, 3.15 ppm, m, 2H, 3.55 ppm, t, J=6 Hz, 2H; 4.50 ppm, t, J=6 Hz, 2H; 5.88 ppm, broad s, 1H, 6.55 ppm, d, J=8 Hz, 1H, 6.82 ppm, d, J=8 Hz, 1H, 7.40 ppm, t, J=8 Hz, 4H, 7.48 ppm, t, J=8 Hz, 2H, 7.72 ppm, d, J=8 Hz, 4H.

EXAMPLE 16

This example refers to reaction H of the process of the invention.

97 g of intermediate (9) obtained as described in example 15 are dissolved in 1 l of THF at room temperature. 86 g of tetrabutylammonium fluoride trihydrate are added to the solution, regulating the temperature so that it does not exceed 40° C. (slightly exothermic reaction). It is kept under agitation for at least one hour at T=25±5° C. checking the progress of the reaction (TLC). 1.5 l of solution saturated with NaCl are prepared separately. At the end of the reaction, the solution of NaCl is poured onto the reaction solution and everything is extracted twice with 1 l of isopropyl acetate. The collected organic phases are washed twice with 1.5 l of water. The organic phase is concentrated to dryness distilling the solvent at reduced pressure and T=45±5° C. Are obtained 89 g of residue which is purified by chromatography on silica gel (heptane:ethyl acetate 8:2). After elimination of the solvent at reduced pressure and T=45±5° C., 35 g of intermediate (10) are obtained of quality suitable for continuation of the synthesis.

A sample of the product thus obtained undergoes $^1$H-NMR and mass analysis obtaining the following result:

Electron impact mass: [M$^+$]=197
$^1$H-NMR (500 MHz, CDCl$_3$): δ (ppm)
3.08 ppm, m, 2H, 3.12 ppm, m, 2H, 3.31 ppm, t, J=8 Hz, 2H, 4.68 ppm, t, J=8 Hz, 2H, 5.46 ppm, non-resolved t, 1H, 6.88 ppm, d, J=8 Hz, 1H, 7.12 ppm, d, J=8 Hz, 1H.

EXAMPLE 17

This example refers to reaction I of the process of the invention.

All the phases of the reaction are performed in an inert atmosphere working with solvents degassed with nitrogen. 890 mg of copper (II) acetate and 3.12 g of Josiphos SL-J001-2 are suspended in 200 ml of toluene and everything is agitated at T=0° C., then 53 ml of diphenylsilane are added. After 45 minutes 32 g of intermediate (10) are added to this suspension, in 200 ml of toluene. Lastly 53 ml of tert-butanol and 80 ml of toluene are added to the resulting suspension. It is kept under agitation at T=0±2° C. checking the progress of the reaction (TLC). At the end of the reaction, maintaining T=0±2° C., the reaction mixture is recovered with 160 ml of aqueous solution of NaOH 2.5 N. It is agitated for approximately 30 minutes allowing the temperature to rise spontaneously to 20° C., then the phases are separated. The aqueous phase is extracted with 250 ml of toluene. The toluenic phase is washed with water (250 ml three times). The organic phase, filtered on a dicalite panel, is evaporated at reduced pressure and T=40±5° C. An orange oil is obtained which, chromatographed on silica gel (heptane:ethyl acetate 9:1) and evaporated to constant weight, provides 27 g of solid.

This product, of quality suitable for continuation of the synthesis, can be crystallised from methanol to provide 23 g of intermediate (XI), the analytical characteristics of which match the product obtained in example 8.

EXAMPLE 18

This example refers to a first possible method of carrying out reaction β$^1$ of the process of the invention.

10 g of product of formula (XI), obtained as described in example 17, are dissolved in 0.5 l of methanol. 410 ml of $NH_3$ in methanol (12.2% w/w) and 12 g of aqueous suspension of Raney nickel are added to the solution. It is hydrogenated at ambient pressure and temperature checking the progress of the reaction every 2 hours. At the end of the reaction (TLC) the catalyst is eliminated by filtration. The solution is concentrated to dryness at reduced pressure. The residue, dissolved in 500 ml of ethyl acetate, is washed twice with an acid solution (100 ml HCl 1 M). The collected aqueous phases are basified to pH>9 with aqueous solution of NaOH. After filtering on card and salting with 55 g of NaCl it is extracted four times with 200 ml of THF. The solvent is distilled at reduced pressure and T=45±5° C. 11 g of yellow solid (intermediate (XII)) are obtained of quality suitable for continuation of the synthesis.

EXAMPLE 19

This example refers to a second possible method of carrying out reaction $\beta^1$ of the process of the invention.

25 g of Raney nickel wet with water are agitated with 200 ml of isopropanol for a few minutes. A large part of the solvent is eliminated by decantation of the solid. The operation is repeated twice. 100 ml of isopropanol, 10 g of intermediate (XI) and 3 g of KOH are then added to the catalyst. The suspension is refluxed for at least two hours checking the progress of the reaction (TLC). At the end of the reaction the catalyst is filtered and the solvent is eliminated, distilling at reduced pressure. The residue is recovered and agitated for 30 minutes at 20° C. with 100 ml of 3 M aqueous hydrochloric acid. An aqueous solution at 10% of NaOH is added up to pH=9. The result is checked by TLC.

50 g of NaCl are added to the reaction mixture and it is then extracted twice with 500 ml of THF. The solvent is distilled at reduced pressure and T=45±5° C. The residue obtained is recovered with 100 ml of HCl in isopropanol (20% by weight). After filtering and drying (reduced P, T=45±5° C.), 7 g of hydrochloride of the intermediate (XII) are obtained.

A sample of the product thus obtained undergoes $^1$H-NMR (DMSO) and mass (electron impact) analysis:

1.6-1.8 ppm, m, 2H; 2.05-2.25 ppm, in, 2H, 2.65-2.90 ppm, m, 4H; 3.05-3.25 ppm, m, 3H, 4.4-4.6 ppm, m, 2H, 6.55 ppm, d, J=8 Hz, 1H, 6.97 ppm, d, J=8 Hz, 1H, 8.00-8.15 ppm broad signal Electron impact mass: $[M^+]$=203; $[M^+]-NH_3$=186

The hydrochloride intermediate (XII), dissolved in water and brought back to free base with NaOH, is compared in high performance thin layer chromatography (HPTLC Silica gel 60 $F_{254}$ glass plates Merck 1.13727.0001) with the intermediate (XII) described in the preceding examples, obtaining complete overlap.

EXAMPLE 20

This example refers to a third possible method of performing reaction $\beta^1$ of the process of the invention.

23 g of intermediate (XI), obtained as described previously, are dissolved in 900 ml of THF at room temperature, in an inert atmosphere (nitrogen). It is then brought to T=0±5° C.

$LiAlH_4$ is added with care, keeping under agitation at T=15° C. The progress of the reaction is checked after at least one hour (TLC). At the end of the reaction ethyl acetate is first added with care, then it is poured into a solution saturated with NaCl ($NaCl_{SS}$) with the addition of ice. The phases are separated, it is re-extracted with ethyl acetate, washed with $NaCl_{ss}$ and anhydrified on sodium sulphate. The solvent is eliminated at reduced pressure and T=45° C., obtaining 20 g of raw intermediate (XII).

EXAMPLE 21

This example refers to a fourth possible method of performing reaction $\beta^1$ of the process of the invention.

10 g of product of formula (XI) obtained as described previously are dissolved in 1 l of THF-ammonia methanol at 5%. 5 g of Pt/C Escat 22 are added to the solution. The suspension is brought to T=65±5° C. and hydrogenated at P=10/12 bar. After 4 h the progress of the reaction is checked (TLC), it is filtered and a further 2.5 g of Pt/C Escat 22 are loaded. The suspension is brought to T=65±5° C. and hydrogenated at P=10/12 bar checking the progress of the reaction (TLC). At the end of the reaction, the catalyst is filtered and the solvent is eliminated at reduced pressure. The residue is recovered and agitated for 30 minutes at 20° C. with 100 ml of 3 M aqueous hydrochloric acid. An aqueous solution at 10% of NaOH is added (cooling to maintain a temperature of approximately 20° C.) until pH=9.50 g of NaCl are added to the reaction mixture and then it is extracted twice with 500 ml of THF. The solvent is distilled at reduced pressure and T=45±5° C. The residue obtained is recovered with 100 ml of HCl in isopropanol (20% by weight). After filtering and drying (reduced P, T=45±5° C.), 5 g of hydrochloride intermediate (XII) are obtained.

EXAMPLE 22

This example refers to reaction $\beta^2$) of the process of the invention—preparation of ramelteon.

10 g of intermediate (XII), obtained as described in example 18, are suspended in 500 ml of THF at room temperature. It is cooled to T=0-5° C. and 13.6 ml of triethylamine and 5.6 ml of propionyl chloride are added. It is agitated allowing the temperature to rise to approximately 25° C. The progress of the reaction is checked after no less than one hour (TLC).

At the end of the reaction, it is cooled to T=0-5° C., 500 ml of water are added and it is extracted with ethyl acetate (500 ml three times). The collected organic phases, washed with aqueous solution saturated with NaCl, are concentrated to dryness by distillation at reduced pressure and T=45° C. The raw ramelteon (13 g) is purified by chromatography on silica gel (heptane:ethyl acetate 4:6) and crystallised with heptane and ethyl acetate as described previously (10.3 g).

EXAMPLE 23

This example refers to reaction H of the process of the invention.

3 g of product of formula (9) obtained as described previously are dissolved in 30 ml of THF at room temperature. 0.179 g of tetrabutylammonium fluoride trihydrate and 0.68 g of KF are added to the solution, regulating the temperature so that it does not exceed 40° C. It is kept under agitation for at least 12 hours at T=25±5° C. in an inert atmosphere checking the progress of the reaction (TLC). At the end of the reaction 30 ml of isopropyl acetate and 45 ml of solution saturated with NaCl are added to the reaction solution. After the phases separate (slow separation), the aqueous phase is re-extracted twice with 25 ml of isopropyl acetate. The organic phases are collected and washed with water. The solvent is eliminated from the organic phase by distillation at reduced pressure, obtaining 2.8 g of solid (single-stain TLC).

The product is crystallised from 11 ml of isopropanol.

EXAMPLE 24

This example refers to reaction H of the process of the invention.

3 g of product of formula (9) obtained as described previously are dissolved in 30 ml of THF at room temperature. 0.178 g of tetrabutylammonium fluoride trihydrate, 10 ml of water and 0.68 g of KF are added to the solution, adjusting the temperature so that it does not exceed 40° C. The reaction mixture has two distinct phases. It is kept under agitation for approximately 3 hours at T=25±5° C. and in an inert atmosphere checking the progress of the reaction (TLC). At the end of the reaction, 10 ml of isopropyl acetate are added to the reaction solution and the phases are separated. The aqueous phase is re-extracted twice with 10 ml of isopropyl acetate. The organic phases are collected and washed with an aqueous solution of NaCl. The solvent is eliminated from the organic phase by distillation at reduced pressure, obtaining 2.5 g of solid (single-stain TLC).

The product is crystallised as described in example 23.

EXAMPLE 25

This example refers to reaction F of the process of the invention.

8.0 g of intermediate (7) are suspended in 80 ml of isopropanol; the suspension is cooled to T=0-5° C. 0.69 g of NaBH$_4$, dissolved in 2 ml of aqueous solution of NaHCO$_3$ at 2.5%, are added slowly to the solution of intermediate (7). The reaction mixture is brought to 25° C. and kept under agitation for approximately 4 hours. At the end of the reaction (TLC control) 80 ml of water containing 1.1 ml of glacial acetic acid are added to the reaction mixture, cooling in order to keep the temperature below 15° C. The precipitation of a pale solid is observed and the formation of a yellow oil along the walls of the flask. The mixture is heated to 45° C. for 30 minutes to crumble the solid and dissolve the oil. 40 ml of water are added and the mixture is cooled in ice for one hour. The solid obtained, isolated by filtration and washed with water (40 ml three times), is dried in a stove under a vacuum at 45° C. for one night, obtaining 7.5 g of intermediate (8) of quality suitable for continuation of the synthesis.

EXAMPLE 26

This example refers to reaction G of the process of the invention.

6.0 g of intermediate (8) are dissolved in 18 ml of pyridine. The mixture is cooled to approximately 5° C., then 2.15 ml of mesyl chloride are added keeping the temperature below 20° C. The reaction mixture, consisting of a suspension, is then brought to 25° C. After approximately 2 hours (TLC control) the reaction mixture is cooled to approximately 5° C. and a further 2.15 ml of mesyl chloride and 6 ml of pyridine are added, keeping the temperature below 20° C. After approximately one hour at 25° C. the reaction is complete (TLC). 120 ml of isopropyl acetate and 108 ml of saturated solution of NaHCO$_3$ are added, cooling in order to keep the temperature below 25° C. The biphasic mixture is filtered on card to isolate the insoluble solid (approximately 2.5 g wet) confirmed by the TLC analysis to be the desired product. The aqueous phase is extracted twice with 72 ml of isopropyl acetate. The solid isolated by filtration is added to the collected organic phases; to obtain complete solubility it is necessary to heat to 45° C. The organic phase, washed three times with 120 ml of 1M HCl and three times with 120 ml of saturated solution of NaCl, is concentrated to dryness at reduced pressure, obtaining 6.8 g of pale solid. The solid is agitated with 14 ml of isopropyl acetate at 45° C. for one hour. 7 ml of heptane are added to the hot suspension, then it is cooled in ice for one hour. The solid, isolated by filtration and washed with 7 ml of cold heptane, is dried in a stove under a vacuum at 45° C.; 6.1 g of intermediate (9) are obtained in the form of a white solid of quality suitable for continuation of the synthesis.

EXAMPLE 27

This example refers to reaction G of the process of the invention.

6.0 g of intermediate (8) are dissolved in 24 ml of pyridine. 5.10 ml (5 mol/mol of substrate) of mesyl chloride (d=1.48 g/ml) are added dropwise, keeping the temperature between 25 and 35° C. The reaction mixture, consisting of a dense but agitable suspension, is then kept at 25-30° C. After 30' the progress of the reaction is checked (TLC). 0.54 ml (0.5 mol/mol of substrate) of mesyl chloride are added dropwise maintaining the temperature between 25 and 35° C. After 30' the reaction is complete. 120 ml of saturated solution of NaHCO$_3$ are added to the reaction mixture, cooling in order to keep the temperature below 20° C. It is checked that it is pH=7. The suspension is agitated at 45° C. for 30' and then cooled in ice for 30'. The solid is isolated by filtration and washed with 28 ml of water, then re-loaded in a reaction flask and dissolved in 175 ml of ethyl acetate. The organic phase is washed with 70 ml of 1M HCl to eliminate the residual pyridine. The organic phase is then washed three times with 70 ml of water, checking that the pH after the last washing is 6-7. The organic phase is concentrated to dryness at reduced pressure, obtaining 6.8 g of pale solid. The solid is recovered with 21 ml of isopropyl acetate at 45° C. for 30'. 14 ml of heptane are added to the hot suspension. The suspension is cooled in ice for one hour. The resulting solid, isolated by filtration and washed with 7 ml of cold heptane containing 4.5% v/v of isopropyl acetate, is dried in a stove under a vacuum at 45° C.; 6.2 g of intermediate (9) are obtained of quality suitable for continuation of the synthesis.

EXAMPLE 28

This example refers to reactions I and g' to produce the intermediate (XII) as a salt of HCl (hydrochloride).

0.829 g of anhydrous copper (II) acetate and 2.923 g of Josiphos SL-J001-2 are suspended in 190 ml of toluene. The suspension is cooled to 0° C., then 49.5 ml of diphenylsilane are added, keeping the temperature at 0-5° C. for a further 45'. 30.0 g of intermediate (10) and 190 ml of toluene are added to the reaction mixture, keeping the temperature at 0-5° C. 50 ml of tert-butanol diluted in 70 ml of toluene are added and it is agitated, keeping the reaction temperature at 0° C. until the end of the reaction. At the end of the reaction (TLC control) a basic aqueous solution is added (18 g of NaOH in 150 ml of water), keeping the temperature at 0° C. The mixture is heated to 20-25° C. and the phases are then separated. The aqueous phase is extracted with 75 ml of toluene. The collected organic phases are washed in sequence: with 240 ml of water containing 27 g of NaCl and 40 ml of 1M HCl, with 240 ml of water containing 27 g of NaCl and with 240 ml of water (the pH of the aqueous phase is approximately 7). The organic phase is treated with 1.5 g of carbon and 3 g of silica and left under agitation for 15' and then filtered on decalite; lastly the panel is washed with toluene.

The organic phase is concentrated to dryness at reduced pressure, obtaining 104.2 g of orange oil which are dissolved in 807 g of solution of ammonia methanol. 20.9 g of Raney Ni (decanted from water) and 650 ml of methanol are added to the solution. Hydrogenation is performed at room temperature and under a slight hydrogen overpressure, monitoring progress by TLC. At the end of the reaction the reaction mixture is filtered on decalite and the panel is washed with methanol. The solution is concentrated to dryness at reduced pressure obtaining 90.7 g of orange oil which is treated with 61 ml of toluene (solution). 6M HCl (25 ml of concentrated HCl diluted with 25 ml of water) is added dropwise to the solution, cooled in ice, in order to keep the temperature below 20° C.: the precipitation of a solid is obtained. The suspension is kept at 0° C. for 30'. The solid is isolated by filtration and washed on the filter with 30 ml of toluene. The wet solid is then pulped at room temperature for 30' in 90 ml of toluene, isolated by filtration and washed with 30 ml of toluene. After drying under a vacuum at 45° C. for approximately 12 h, 29.9 g of hydrochloride intermediate (XII) are obtained of quality suitable for continuation of the synthesis.

This intermediate can be further purified with acetone. The hydrochloride intermediate (XII), suspended in 320 ml of acetone, is agitated at 20/25° C. for 30 minutes before being filtered. After drying at 45° C. and reduced pressure for approximately 12 hours, 24 g of hydrochloride intermediate (XII) are obtained.

EXAMPLE 29

This example refers to the preparation of ramelteon from the hydrochloride intermediate (XII) via reaction $\beta^2$ of the process of the invention.

The operation is performed under a nitrogen flow. 15 g of hydrochloride intermediate (XII) are suspended in 450 ml of THF. 31 ml of TEA are added to the suspension and everything is cooled to 0° C. 7.2 ml of propionyl chloride are added to the reaction mixture, keeping the temperature below 15° C. The suspension is brought to 20-25° C. and agitated at said temperature until the end of the reaction (TLC control). The reaction mixture is cooled to 0° C. and 240 ml of water and 150 ml of isopropyl acetate are added, keeping the temperature below 15° C. The phases are separated and the aqueous phase is extracted with 150 ml of isopropyl acetate. The collected organic phases are washed with 240 ml of water containing 42.5 g of NaCl. The organic phase is concentrated at reduced pressure to dryness, obtaining 16.2 g of raw ramelteon which is then purified as described in the preceding examples or as already described in literature.

EXAMPLE 30

This example refers to the preparation of ramelteon from the hydrochloride intermediate (XII) via reaction $\beta^2$ of the process of the invention.

25 g of hydrochloride intermediate (XII) are suspended in 63 ml of THF. 88 ml of water are added to the suspension, obtaining complete dissolution. 31.4 g of aqueous solution of NaOH at 30% are then added to the reaction mixture, obtaining a biphase solution. Keeping the reaction temperature between 20 and 25° C., 15.5 ml of propionic anhydride are added and, after the addition, it is agitated at the same temperature for 1 hour checking the end of the reaction (TLC). At the end of the reaction, it is cooled to T=10° C. and 200 ml of water are added. The suspension is cooled and agitated for at least 2 hours at T=0° C. The solid obtained is filtered and washed with water. After drying at reduced pressure for at least 12 hours at T=45° C., 26.9 g of ramelteon (white solid) are obtained.

If the hydrochloride intermediate XII used has been previously crystallised by the water-isopropanol mixture, the ramelteon obtained has HPLC titer greater than 99% and enantiomeric excess greater than 99.9%. The purity of the product can be further increased by performing the purifications described in the preceding examples and in the literature.

What is claimed is:

1. Process for the preparation of N-[2-(8S)-1,6,7,8-tetrahydro-2H-indeno[5,4-b]furan-8-yl]ethyl]propionamide (ramelteon), of formula (I)

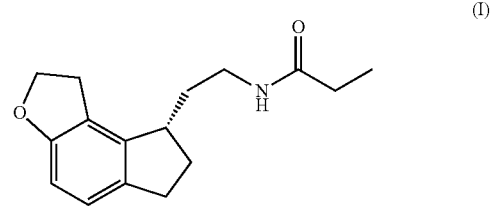

(I)

comprising the following reactions:
a) alkylation of the hydroxyl of 6-hydroxy-indanone (compound (II)), to obtain the intermediate (III), 6-allyloxy-indan-1-one:

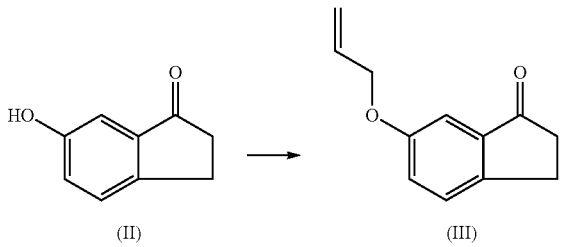

b) thermal Claisen rearrangement on the intermediate (III) to obtain the intermediate (IV), 7-allyl-6-hydroxy-indan-1-one:

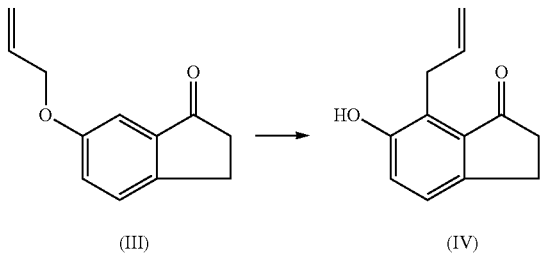

c) protection of the free hydroxyl of the intermediate (IV) to obtain an intermediate of formula (V):

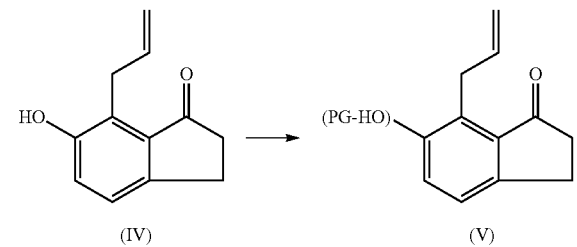

wherein (PG-OH) indicates the hydroxyl group protected with a protective group stable in a basic environment;

d) reaction of the intermediate (V) to obtain an intermediate of formula (VI):

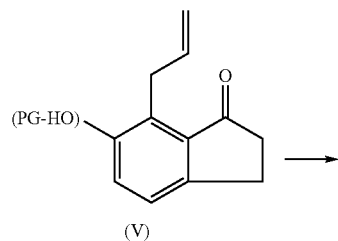

(V)

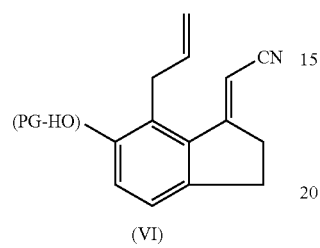

(VI)

-) transformation of the intermediate (VI) into the intermediate (XI), (1,6,7,8-tetrahydro-2H-indeno[5,4-b]furan-8-yl)acetonitrile:

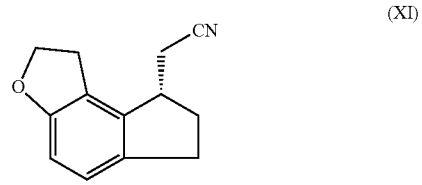

(XI)

-) transformation of the intermediate (XI) into ramelteon:

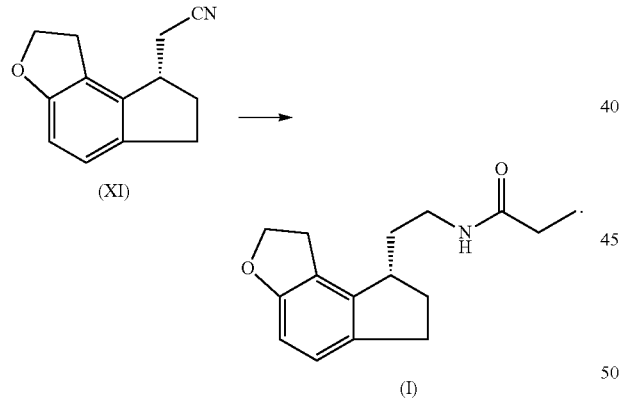

2. Process according to claim 1, wherein said transformation of the intermediate (VI) into intermediate (XI) comprises the following reactions:

e) stereospecific reduction on the intermediate (VI) to obtain an intermediate of formula (VII):

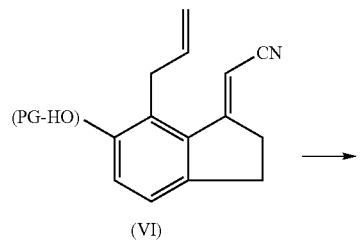

(VI)

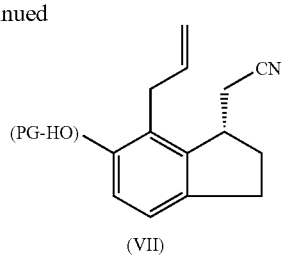

(VII)

f) oxidative demolition of the double bond of the intermediate (VII) to obtain an intermediate of formula (VIII):

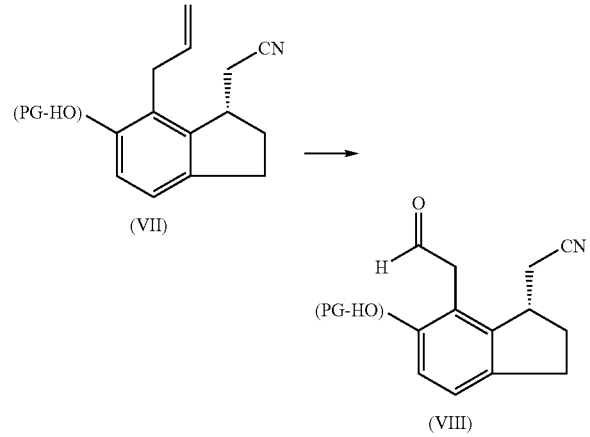

g) reduction of the carbonylic function of the intermediate (VIII) to obtain an intermediate of formula (IX):

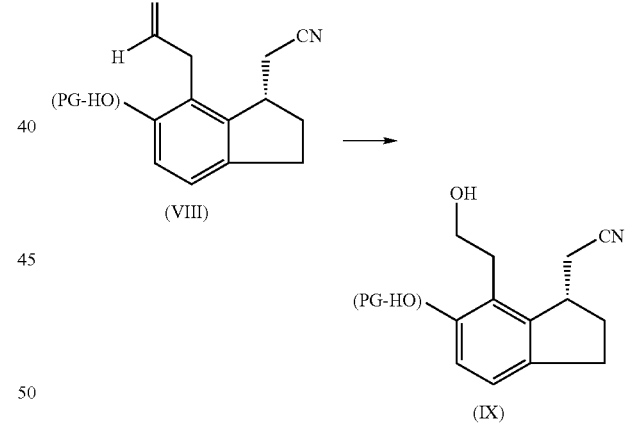

h) transformation of the free hydroxyl group present in the intermediate (IX) in order to make it a good leaving group, to obtain an intermediate with general formula (X), wherein (LG) indicates the leaving group:

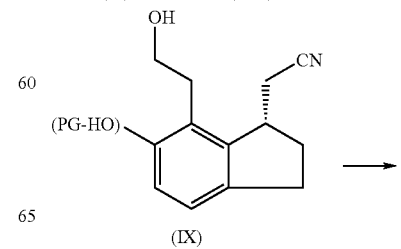

(IX)

-continued

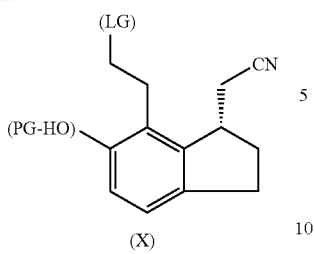

i) intramolecular cyclisation of the intermediate (X) to obtain the intermediate (XI):

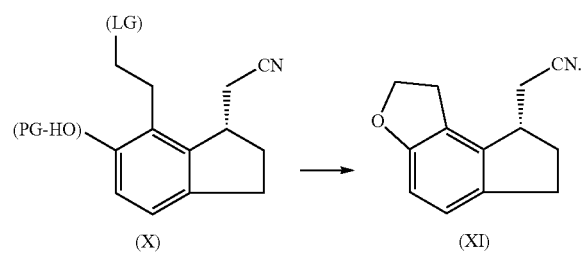

3. Process according to claim 1, wherein said transformation of the intermediate (VI) into intermediate (XI) comprises the following reactions:

E) selective oxidative demolition of the terminal double bond on the intermediate (VI) to obtain an intermediate of formula (7):

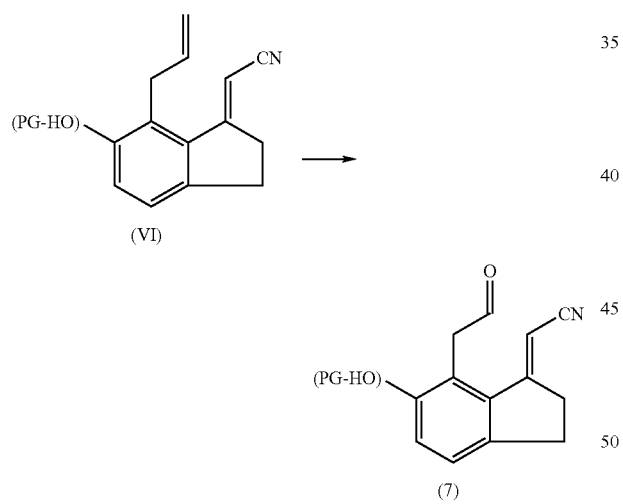

F) reduction of the carbonylic function present in the intermediate (7) to obtain an intermediate of formula (8):

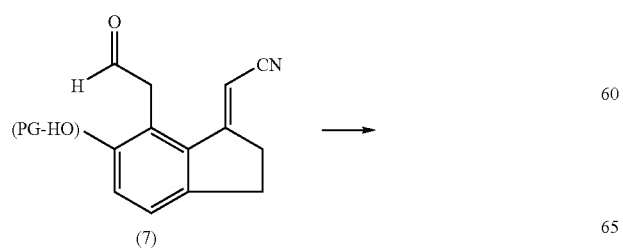

-continued

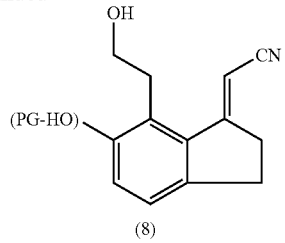

G) transformation of the free hydroxyl group of the intermediate (8), in order to make it a good leaving group, to obtain the intermediate (9), wherein (LG) indicates the leaving group:

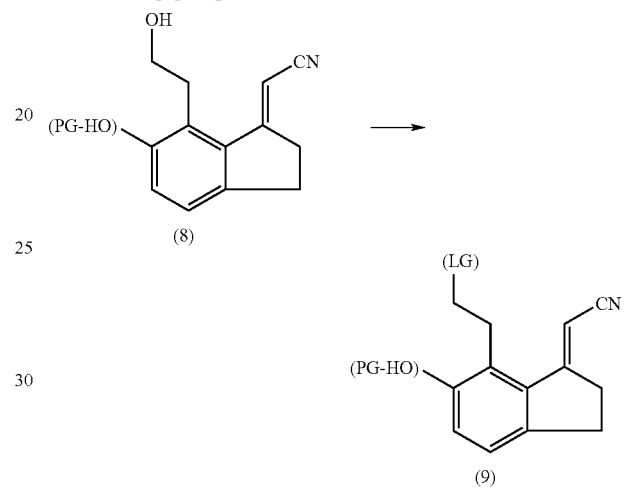

H) intramolecular cyclisation of the intermediate (9) to obtain the intermediate (10), (1,6,7,8-tetrahydro-2H-indeno[5,4-b]furan-8-ylidene)acetonitrile:

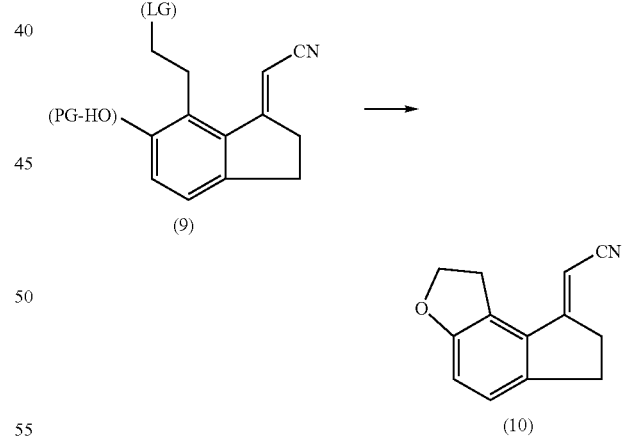

I) stereospecific reduction on the intermediate (10) to obtain the intermediate (XI):

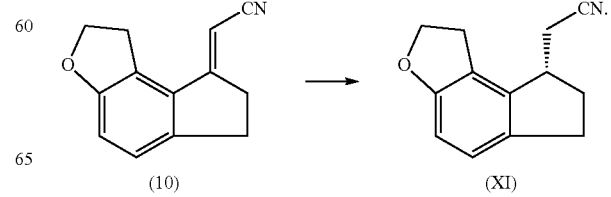

4. Process according to claim 1, wherein said transformation into ramelteon of the intermediate (XI) occurs in one single reaction α) by direct hydrogenation of the triple bond of the group —C≡N of said intermediate (XI) in the presence of propionic anhydride or propionic acid:

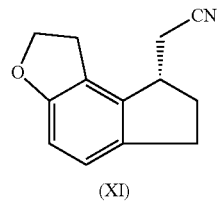

(XI)

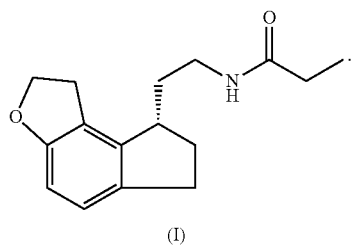

(I)

5. Process according to claim 1, wherein said transformation into ramelteon of the intermediate (XI) occurs in two stages, a first reaction β¹) for reduction of the triple bond of the group —C≡N of said intermediate (XI) to group —CH₂NH₂ to obtain the intermediate (XII), 2-(1,6,7,8-tetrahydro-2H-indeno[5,4-b]furan-8-yl)ethylamine, and a second reaction β²) for treatment of the intermediate (XII) with propionic acid, propionic anhydride or propionyl chloride:

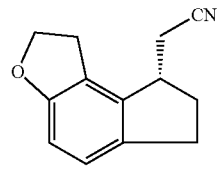

(XI)

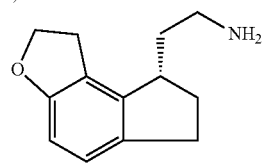

(XII)

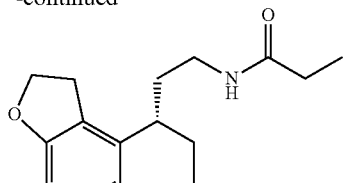

(I)

6. Process according to claim 2, wherein the enantioselective reduction reaction e is performed in an inert atmosphere without oxygen, in a solvent inert in the reaction conditions, at a temperature between −5 and +20° C., by chemical reduction of said intermediate (VI) in the presence of the ethanol adduct of (S)-1-[(R)-2-diphenylphosphino)ferrocenyl]ethyldicyclohexylphosphine, copper (II) acetate, a silane and tert-butanol.

7. Process according to claim 3, wherein the enantioselective reduction reaction I is performed in an inert atmosphere without oxygen, in a solvent inert in the reaction conditions, at a temperature between −5 and +20° C., by chemical reduction of said intermediate (10) in the presence of the ethanol adduct of (S)-1-[(R)-2-diphenylphosphino)ferrocenyl]ethyldicyclohexylphosphine, copper (II) acetate, a silane and tert-butanol.

8. Process according to claim 6 wherein said ethanol adduct of (S)-1-[(R)-2-diphenylphosphino)ferrocenyl]ethyldicyclohexylphosphine is used in a molar quantity of between 0.1 and 6%, with respect to the quantity of intermediate (VI) or (10).

9. Process according to claim 7 wherein said ethanol adduct of (S)-1-[(R)-2-diphenylphosphino)ferrocenyl]ethyldicyclohexylphosphine is used in a molar quantity of between 0.1 and 6%, with respect to the quantity of intermediate (VI) or (10).

10. Process according to claim 6, wherein said temperature is between 0 and 5° C.

11. Process according to claim 7, wherein said temperature is between 0 and 5° C.

12. Process according to claim 8, wherein said molar quantity is between 1 and 5%.

13. Process according to claim 9, wherein said molar quantity is between 1 and 5%.

* * * * *